US011865166B2

United States Patent
Weiner et al.

(10) Patent No.: US 11,865,166 B2
(45) Date of Patent: Jan. 9, 2024

(54) NUCLEIC ACID ENCODING OPTIMIZED IMMUNOGENIC PEPTIDE THAT TARGETS FOLLICLE STIMULATING HORMONE RECEPTOR

(71) Applicants: The Trustees of the University of Pennsylvania, Philadelphia, PA (US); Inovio Pharmaceuticals, Inc., Plymouth Meeting, PA (US); THE WISTAR INSTITUTE OF ANATOMY AND BIOLOGY, Philadelphia, PA (US)

(72) Inventors: David Weiner, Merion, PA (US); Alfredo Perales Puchalt, Philadelphia, PA (US); Jian Yan, Wallingford, PA (US); Anna Maria Slager, Lansdale, PA (US)

(73) Assignees: The Trustees of the University of Pennsylvania, Philadelphia, PA (US); Inovio Pharmaceuticals, Inc., Plymouth Meeting, PA (US); The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 16/328,404

(22) PCT Filed: Aug. 29, 2017

(86) PCT No.: PCT/US2017/049186
§ 371 (c)(1),
(2) Date: Feb. 26, 2019

(87) PCT Pub. No.: WO2018/044929
PCT Pub. Date: Mar. 8, 2018

(65) Prior Publication Data
US 2019/0192644 A1 Jun. 27, 2019

Related U.S. Application Data

(60) Provisional application No. 62/380,766, filed on Aug. 29, 2016.

(51) Int. Cl.
C07H 21/02 (2006.01)
A61K 39/00 (2006.01)
A61K 38/17 (2006.01)
A61P 35/00 (2006.01)
C07K 14/72 (2006.01)

(52) U.S. Cl.
CPC .. A61K 39/001102 (2018.08); A61K 38/1796 (2013.01); A61K 39/0011 (2013.01); A61P 35/00 (2018.01); C07K 14/723 (2013.01); A61K 2039/5256 (2013.01); A61K 2039/53 (2013.01); A61K 2039/572 (2013.01); A61K 2039/892 (2018.08)

(58) Field of Classification Search
None
See application file for complete search history.

(56) References Cited

U.S. PATENT DOCUMENTS

2002/0061557 A1 * 5/2002 Nikolics ............ C07K 16/2869
514/19.5

FOREIGN PATENT DOCUMENTS

| WO | 1993020199 | 10/1993 | |
|---|---|---|---|
| WO | WO-2006109696 A1 * | 10/2006 | ............. C07K 14/59 |
| WO | 2016073456 | 5/2016 | |
| WO | WO-2016073456 A1 * | 5/2016 | ............. A61K 35/17 |

OTHER PUBLICATIONS (Biophys. Res. Commun. 275: 121-128, 2000 (Year: 2000).*
Miosge (Proc Natl Acad Sci US A. Sep. 15, 2015;112(37): E5189-98) (Year: 2015).*
Perales-Puchalt et al., "Follicle-Stimulating Hormone Receptor is Expressed by Most Ovarian Cancer Subtypes and is a Safe and Effective Immunotherapeutic Target," Clinical Cancer Research, 2017, 23(3):441-453.
Bagarazzi et al., "Immunotherapy against HPV16/18 generates potent TH1 and cytotoxic cellular immune responses," Sci Transl Med. 2012, 4:155ra38, 33 pages.
Kalams et al., "Safety and comparative immunogenicity of an HIV-1 DNA vaccine in combination with plasmid interleukin 12 and impact of intramuscular electroporation for delivery," J Infect Dis. 2013, 208:818-829.
Morrow et al., "Synthetic Consensus HIV-1 DNA Induces Potent Cellular Immune Responses and Synthesis of Granzyme B, Perforin in HIV Infected Individuals," Mol Ther. 2015, 23:591-601.
Flingai et al., "Synthetic DNA Vaccines: Improved Vaccine Potency by Electroporation and Co-Delivered Genetic Adjuvants," Front Immunol. 2013, 4:354, 10 pages.
Sardesai and Weiner, "Electroporation delivery of DNA vaccines: prospects for success," Curr Opin Immunol. 2011, 23:421-429.
Zhang et al., "Follicle-Stimulating Hormone Peptide can Facilitate Paclitaxel Nanoparticles to Target Ovarian Carcinoma In vivo," Cancer Res. 2009, 69:6506-6514.
Al-Timimi et al., "An immunohistochemical study of the incidence and significance of human gonadotrophin and prolactin binding sites in normal and neoplastic human ovarian tissue," Br J Cancer, 1986, 53:321-329.
Minegishi et al., "Expression of gonadotropin and activin receptor messenger ribonucleic acid in human ovarian epithelial neoplasms," Clin Cancer Res. 2000, 6:2764-2770.
Zheng et al., "Ovarian Epithelial Tumor Growth Promotion by Follicle-Stimulating Hormone and Inhibition of the Effect by Luteinizing Hormone," Gynecol Oncol. 2000, 76:80-88.
Kutzler and Weiner, "Developing DNA vaccines that call to dendritic cells," J Clin Invest. 2004, 114:1241-1244.

(Continued)

Primary Examiner — Michael C Wilson
(74) Attorney, Agent, or Firm — Riverside Law LLP

(57) ABSTRACT

Provided herein is an immunogenic composition comprising a synthetic consensus antigen to Follicle Stimulating Hormone Receptor (FSHR) protein which is abundant in many ovarian cancer sub-types. Also disclosed herein is a method of treating a tumor associated pathology in a subject in need thereof, by administering the immunogenic composition to the subject.

12 Claims, 13 Drawing Sheets
Specification includes a Sequence Listing.

(56) References Cited

OTHER PUBLICATIONS

Villarreal et al., "Ubiquitin-like molecule ISG15 acts as an immune adjuvant to enhance antigen-specific CD8 T-cell tumor immunity," Mol Ther. 2015, 23:1653-1662.

Villarreal et al., "Molecular adjuvant IL-33 enhances the potency of a DNA vaccine in a lethal challenge model," Vaccine, 2015, 33:4313-4320.

Villarreal et al., "Alarmin IL-33 Acts as an Immunoadjuvant to Enhance Antigen-Specific Tumor Immunity," Cancer Res. 2014, 74:1789-1800.

Hamanishi et al., "Safety and antitumor activity of anti-PD-1 antibody, nivolumab, in patients with platinum-resistant ovarian cancer," J Clin Oncol. 2015, 33:4015-4022.

Brahmer et al., "Safety and activity of anti-PD-L1 antibody in patients with advanced cancer," N Engl J Med. 2012, 366:2455-2465.

Hodi et al., "Biologic activity of cytotoxic T lymphocyte-associated antigen 4 antibody blockade in previously vaccinated metastatic melanoma and ovarian carcinoma patients," Proc Natl Acad Sci U.S.A. 2003, 100:4712-4717.

* cited by examiner

NUCLEIC ACID ENCODING OPTIMIZED IMMUNOGENIC PEPTIDE THAT TARGETS FOLLICLE STIMULATING HORMONE RECEPTOR

CROSS-REFERENCE TO RELATED APPLICATIONS

This application is a U.S. national phase application filed under 35 U.S.C. § 371 claiming priority to International Patent Application No. PCT/US17/049186, filed Aug. 29, 2017, which is entitled to priority to U.S. Provisional Application No. 62/380,766, filed Aug. 29, 2016, the contents of each of which are incorporated by reference herein in their entireties.

TECHNICAL FIELD

The present invention relates to immunogenic compositions targeting Follicle Stimulating Hormone Receptor (FSHR), and methods of administering the immunogenic compositions.

BACKGROUND OF THE INVENTION

Epithelial ovarian cancer is one of the deadliest tumors, killing>14,000 women each year in the U.S. Despite advances in surgical approach and chemotherapy, 5-year survival rates have barely changed in the last 40 years. Ovarian cancer is an immunogenic tumor, and T-cell infiltration has been repeatedly been associated with a better prognosis (Zhang et al., N Engl J Med. 2003, 348:203-213). However, only around 50% of tumors present with infiltrating T-cells (Zhang et al., N Engl J Med. 2003, 348:203-213). Immunotherapies aimed to enhance ovarian cancer T-cell infiltration could therefore have a big impact in reversing this dismal prognosis.

The follicle-stimulating hormone receptor (FSHR) is an antigen that is selectively expressed in women in the ovarian granulosa cells (Simoni et al., Endocr Rev. 1997, 18:739-773) and at low levels in the ovarian endothelium (Vannier et al., Biochemistry, 1996, 35:1358-1366). Most importantly, this surface antigen is expressed in 50-70% of ovarian carcinomas (Perales-Puchalt et al., Clin Cancer Res. 2016; Zhang et al., Cancer Res. 2009, 69:6506-6514; Al-Timimi et al., Br J Cancer, 1986, 53:321-329; Minegishi et al., Clin Cancer Res. 2000, 6:2764-2770; Zheng et al., Gynecol Oncol. 2000, 76:80-88) and not in non-gonadal healthy tissues, including the brain where negative feedback is dependent on estrogen. Given that oophorectomy is a standard procedure in the treatment of ovarian cancer, redirecting the immune system against the FSHR should not cause damage to healthy tissues. Previous studies have redirected T-cells with chimeric receptors against FSHR with no noticeable toxicity. Therefore, FSHR could be an ideal therapeutic target for the generation of a synthetic consensus DNA vaccine that would redirect T cells against ovarian cancer.

Historically, peptide vaccination has shown good cellular responses, especially in murine models (Parmiani et al., J Natl Cancer Inst. 2002, 94:805-818). However, recent improvements in plasmid design and delivery have led to impressive CD8 and CD4 T-cell responses from new synthetic DNA approaches in humans (Bagarazzi et al., Sci Transl Med. 2012, 4:155ra38; Kalams et al., J Infect Dis. 2013, 208:818-829; Morrow et al., Mol Ther. 2015, 23:591-601). Synthetic DNA vaccines, unlike peptide vaccines, are not HLA restricted and are robustly presented on MHCI and MHCII, and can be designed to drive class II responses and therefore break tolerance (Flingai et al., Front Immunol. 2013, 4:354; Sardesai and Weiner, Curr Opin Immunol. 2011, 23:421-429).

Breaking immune tolerance to FSHR has the potential to improve cancer therapy. Thus, there is a need in the art for the development of vaccines directed at FSHR capable of breaking tolerance. The present invention satisfies this unmet need.

SUMMARY OF THE INVENTION

In one embodiment, the invention relates to an immunogenic composition comprising a nucleic acid molecule, wherein the nucleic acid molecule encodes a peptide comprising an amino acid sequence of a) an amino acid sequence having at least about 90% identity over an entire length of the amino acid sequence selected from the group consisting of SEQ ID NO:2, SEQ ID NO:6 and SEQ ID NO:10, b) an immunogenic fragment comprising at least about 90% identity over at least 60% of the amino acid sequence selected from the group consisting of SEQ ID NO:2, SEQ ID NO:6 and SEQ ID NO:10, c) the amino acid sequence selected from the group consisting of SEQ ID NO:2, SEQ ID NO:6 and SEQ ID NO:10, or d) an immunogenic fragment comprising at least 60% of the amino acid sequence selected from the group consisting of SEQ ID NO:2, SEQ ID NO:6 and SEQ ID NO:10.

In one embodiment, the nucleic acid molecule is a DNA molecule or an RNA molecule.

In one embodiment, the nucleic acid molecule comprises a nucleotide sequence of a) a nucleotide sequence having at least about 90% identity over an entire length of a nucleotide sequence selected from the group consisting of SEQ ID NO:1, SEQ ID NO:5 and SEQ ID NO:9, b) an immunogenic fragment of a nucleotide sequence having at least about 90% identity over at least 60% of the nucleotide sequence selected from the group consisting of SEQ ID NO:1, SEQ ID NO:5 and SEQ ID NO:9, c) a nucleotide sequence selected from the group consisting of SEQ ID NO:1, SEQ ID NO:5 and SEQ ID NO:9, or d) an immunogenic fragment of a nucleotide sequence selected from the group consisting of SEQ ID NO:1, SEQ ID NO:5 and SEQ ID NO:9.

In one embodiment, the encoding nucleotide sequence is operably linked to at least one regulatory sequence selected from the group consisting of a start codon, a nucleotide sequence encoding an IgE leader sequence and a stop codon.

In one embodiment, the nucleic acid molecule encodes a peptide comprising an amino acid sequence of a) an amino acid sequence having at least about 90% identity over an entire length of the amino acid sequence selected from the group consisting of SEQ ID NO:4, SEQ ID NO:8 and SEQ ID NO:12, b) an immunogenic fragment comprising at least about 90% identity over at least 60% of the amino acid sequence selected from the group consisting of SEQ ID NO:4, SEQ ID NO:8 and SEQ ID NO:12, c) the amino acid sequence selected from the group consisting of SEQ ID NO:4, SEQ ID NO:8 and SEQ ID NO:12, or d) an immunogenic fragment comprising at least 60% of the amino acid sequence selected from the group consisting of SEQ ID NO:4, SEQ ID NO:8 and SEQ ID NO:12.

In one embodiment, the nucleic acid molecule comprises a nucleotide sequence of a) a nucleotide sequence having at least about 90% identity over an entire length of a nucleotide sequence selected from the group consisting of SEQ ID NO:3, SEQ ID NO:7 and SEQ ID NO:11, b) an immunogenic fragment of a nucleotide sequence having at least about 90% identity over at least 60% of the nucleotide sequence selected from the group consisting of SEQ ID NO:3, SEQ ID NO:7 and SEQ ID NO:11, c) a nucleotide sequence selected from the group consisting of SEQ ID NO:3, SEQ ID NO:7 and SEQ ID NO:11, or d) an immunogenic fragment of a nucleotide sequence selected from the group consisting of SEQ ID NO:3, SEQ ID NO:7 and SEQ ID NO:11.

In one embodiment, the nucleic acid molecule is an expression vector.

In one embodiment, the nucleic acid molecule is a viral particle.

In one embodiment, the immunogenic composition comprises a pharmaceutically acceptable excipient.

In one embodiment, the immunogenic composition comprises an adjuvant.

In one embodiment, the invention relates to a nucleic acid molecule encoding a peptide comprising an amino acid sequence of a) an amino acid sequence having at least about 90% identity over an entire length of the amino acid sequence selected from the group consisting of SEQ ID NO:2, SEQ ID NO:6 and SEQ ID NO:10, b) an immunogenic fragment comprising at least about 90% identity over at least 60% of the amino acid sequence selected from the group consisting of SEQ ID NO:2, SEQ ID NO:6 and SEQ ID NO:10, c) the amino acid sequence selected from the group consisting of SEQ ID NO:2, SEQ ID NO:6 and SEQ ID NO:10, or d) an immunogenic fragment comprising at least 60% of the amino acid sequence selected from the group consisting of SEQ ID NO:2, SEQ ID NO:6 and SEQ ID NO:10.

In one embodiment, the nucleic acid molecule is selected from the group consisting of a DNA molecule and an RNA molecule.

In one embodiment, the nucleic acid molecule comprises a nucleotide sequence of a) a nucleotide sequence having at least about 90% identity over an entire length of a nucleotide sequence selected from the group consisting of SEQ ID NO:1, SEQ ID NO:5 and SEQ ID NO:9, b) an immunogenic fragment of a nucleotide sequence having at least about 90% identity over at least 60% of the nucleotide sequence selected from the group consisting of SEQ ID NO:1, SEQ ID NO:5 and SEQ ID NO:9, c) a nucleotide sequence selected from the group consisting of SEQ ID NO:1, SEQ ID NO:5 and SEQ ID NO:9, or d) an immunogenic fragment of a nucleotide sequence selected from the group consisting of SEQ ID NO:1, SEQ ID NO:5 and SEQ ID NO:9.

In one embodiment, the nucleotide sequence is operably linked to at least one of a start codon, a nucleotide sequence encoding an IgE leader sequence and a stop codon.

In one embodiment, the nucleic acid molecule encodes a peptide comprising an amino acid sequence of a) an amino acid sequence having at least about 90% identity over an entire length of the amino acid sequence selected from the group consisting of SEQ ID NO:4, SEQ ID NO:8 and SEQ ID NO:12, b) an immunogenic fragment comprising at least about 90% identity over at least 60% of the amino acid sequence selected from the group consisting of SEQ ID NO:4, SEQ ID NO:8 and SEQ ID NO:12, c) the amino acid sequence selected from the group consisting of SEQ ID NO:4, SEQ ID NO:8 and SEQ ID NO:12, or d) an immunogenic fragment comprising at least 60% of the amino acid sequence selected from the group consisting of SEQ ID NO:4, SEQ ID NO:8 and SEQ ID NO:12.

In one embodiment, the nucleic acid molecule comprises a nucleotide sequence of a) a nucleotide sequence having at least about 90% identity over an entire length of a nucleotide sequence selected from the group consisting of SEQ ID NO:3, SEQ ID NO:7 and SEQ ID NO:11, b) an immunogenic fragment of a nucleotide sequence having at least about 90% identity over at least 60% of the nucleotide sequence selected from the group consisting of SEQ ID NO:3, SEQ ID NO:7 and SEQ ID NO:11, c) a nucleotide sequence selected from the group consisting of SEQ ID NO:3, SEQ ID NO:7 and SEQ ID NO:11, or d) an immunogenic fragment of a nucleotide sequence selected from the group consisting of SEQ ID NO:3, SEQ ID NO:7 and SEQ ID NO:11.

In one embodiment, the nucleic acid molecule is an expression vector.

In one embodiment, the nucleic acid molecule is a viral particle.

In one embodiment, the invention relates to an immunogenic composition comprising a peptide, wherein the peptide comprises an amino acid sequence of a) an amino acid sequence having at least about 90% identity over an entire length of the amino acid sequence selected from the group consisting of SEQ ID NO:2, SEQ ID NO:4, SEQ ID NO:6 and SEQ ID NO:8, b) an immunogenic fragment comprising at least about 90% identity over at least 60% of the amino acid sequence selected from the group consisting of SEQ ID NO:2, SEQ ID NO:4, SEQ ID NO:6 and SEQ ID NO:8, c) the amino acid sequence as selected from the group consisting of SEQ ID NO:2, SEQ ID NO:4, SEQ ID NO:6 and SEQ ID NO:8 or d) an immunogenic fragment comprising at least 60% of the amino acid sequence selected from the group consisting of SEQ ID NO:2, SEQ ID NO:4, SEQ ID NO:6 and SEQ ID NO:8.

In one embodiment, the invention relates to a peptide comprising an amino acid sequence of a) an amino acid sequence having at least about 90% identity over an entire length of the amino acid sequence set forth in SEQ ID NO:2, SEQ ID NO:4, SEQ ID NO:6, SEQ ID NO:8, SEQ ID NO:10 or SEQ ID NO:12, b) an immunogenic fragment comprising at least about 90% identity over at least 60% of the amino acid sequence set forth in SEQ ID NO:2, SEQ ID NO:4, SEQ ID NO:6, SEQ ID NO:8, SEQ ID NO:10 or SEQ ID NO:12, c) the amino acid sequence as set forth in SEQ ID NO:2, SEQ ID NO:4, SEQ ID NO:6, SEQ ID NO:8, SEQ ID NO:10 or SEQ ID NO:12, or d) an immunogenic fragment comprising at least 60% of the amino acid sequence set forth in SEQ ID NO:2, SEQ ID NO:4, SEQ ID NO:6, SEQ ID NO:8, SEQ ID NO:10 or SEQ ID NO:12.

In one embodiment, the invention relates to a method of inducing an immune response against Follicle Stimulating Hormone Receptor (FSHR) in a subject in need thereof, the method comprising administering to the subject an immunogenic composition comprising a nucleic acid molecule, wherein the nucleic acid molecule encodes a peptide comprising an amino acid sequence of a) an amino acid sequence having at least about 90% identity over an entire length of the amino acid sequence selected from the group consisting of SEQ ID NO:2, SEQ ID NO:6 and SEQ ID NO:10, b) an immunogenic fragment comprising at least about 90% identity over at least 60% of the amino acid sequence selected from the group consisting of SEQ ID NO:2, SEQ ID NO:6 and SEQ ID NO:10, c) the amino acid sequence selected from the group consisting of SEQ ID NO:2, SEQ ID NO:6 and SEQ ID NO:10, or d) an immunogenic fragment comprising at least 60% of the amino acid sequence selected from the group consisting of SEQ ID NO:2, SEQ ID NO:6 and SEQ ID NO:10. In one embodiment, the method of administering includes at least one of electroporation and injection.

In one embodiment, the invention relates to a method of treating or preventing a tumor associated pathology in subject in need thereof, the method comprising administering to the subject an immunogenic composition comprising a nucleic acid molecule, wherein the nucleic acid molecule encodes a peptide comprising an amino acid sequence of a) an amino acid sequence having at least about 90% identity over an entire length of the amino acid sequence selected from the group consisting of SEQ ID NO:2, SEQ ID NO:6 and SEQ ID NO:10, b) an immunogenic fragment comprising at least about 90% identity over at least 60% of the amino acid sequence selected from the group consisting of SEQ ID NO:2, SEQ ID NO:6 and SEQ ID NO:10, c) the amino acid sequence selected from the group consisting of SEQ ID NO:2, SEQ ID NO:6 and SEQ ID NO:10, or d) an immunogenic fragment comprising at least 60% of the amino acid sequence selected from the group consisting of SEQ ID NO:2, SEQ ID NO:6 and SEQ ID NO:10. In one embodiment, the method of administering includes at least one of electroporation and injection.

In one embodiment, a tumor associated pathology is at least one of tumor growth, tumor metastasis, and angiogenesis.

In one embodiment, the subject has been diagnosed with cancer.

In one embodiment, the cancer is ovarian cancer.

In one embodiment, the method further comprises administering an immunogenic composition comprising one or more ovarian cancer antigens to the subject.

In one embodiment, the subject is at high risk of developing cancer.

In one embodiment, the cancer is ovarian cancer.

In one embodiment, the method further comprises administering an immunogenic composition comprising one or more ovarian cancer antigens to the subject.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts FSHR expression of 404 cases of ovarian cancer from The Cancer Genome Atlas (TCGA) dataset. FIG. 1B depicts a representative immunohistochemistry image of a mucinous ovarian cancer stained for FSHR. FIG. 1C depicts normalized real-time quantitative-PCR of FSHR expression in human healthy tissues (Perales-Puchalt et al., Clin Cancer Res. 2016).

FIG. 3, comprising FIG. 3A depicts a diagram of the experimental design. Five mice were vaccinated in each group. FIG. 3B depicts exemplary experimental results demonstrating that immunization with syncon FSHR induces a greater IFNγ response against consensus FSHR peptides than immunization with native FSHR. FIG. 3C depicts exemplary experimental results demonstrating that immunization with syncon FSHR induces a greater IFNγ response against native FSHR peptides than immunization with native FSHR.

FIG. 12, comprising FIG. 12A depicts a diagram of the experimental design. FIG. 12B depicts the results of an exemplary experiment evaluating the total tumor associated fluorescence of immunized mice following tumor transplantation. FIG. 12C depicts images of tumor growth in immunized mice following tumor transplantation.

DETAILED DESCRIPTION

Figures 1A, 1B, 1C:
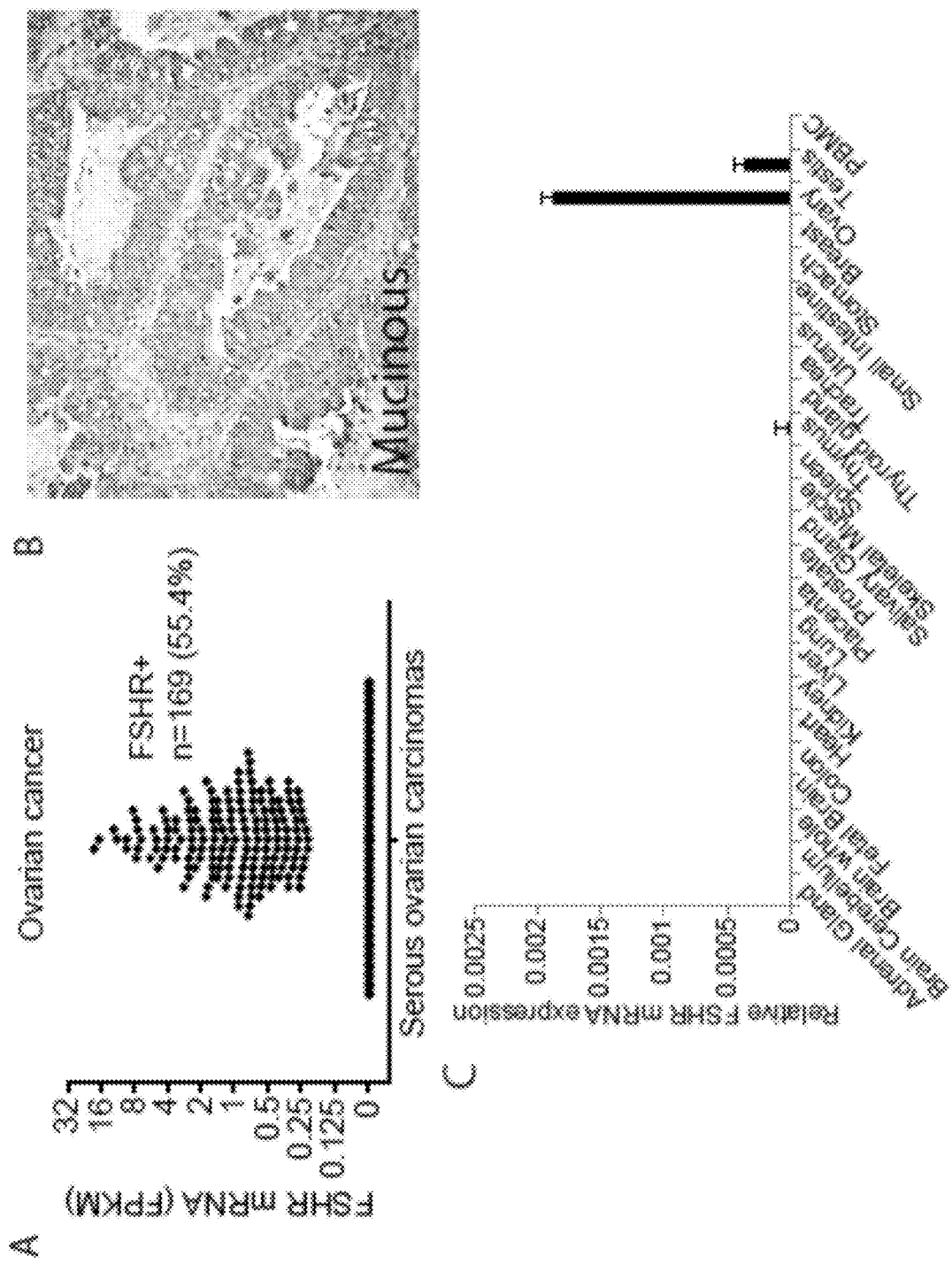
FIG. 1A through FIG. 1C, depicts results demonstrating that FSHR is expressed in approximately 50% of ovarian cancers but not in non-gonadal healthy adult tissues.

In one aspect, the present invention provides an immunogenic composition targeting FSHR antigen. Further aspects of the present invention are treatments and/or preventions of cancer growth or metastasis using the disclosed immunogenic composition alone or in combination with additional cancer vaccines or therapeutics.

The sequence encoding the FSHR antigen of the invention is genetically diverged from the sequence encoding the native FSHR protein, and thus, the antigen of the invention is unique. The immunogenic composition of the present invention can be widely applicable to breaking tolerance to the native antigen, and reducing or preventing tumor growth or metastasis because of the unique sequences of the encoded antigen. These unique sequences allow the immunogenic composition to be protective against multiple types of cancer.

The immunogenic composition can be used to protect against and treat any number of cancers. The immunogenic composition can elicit both humoral and cellular immune responses that target the antigen. The immunogenic composition can elicit neutralizing antibodies and immunoglobulin G (IgG) antibodies that are reactive with the antigen. The immunogenic composition can also elicit a CD8$^+$ T cell response that is reactive to the antigen and produce one or more of interferon-gamma (IFN-$\gamma$) and tumor necrosis factor alpha (TNF-$\alpha$). In one embodiment, the immunogenic composition can also elicit a CD4$^+$ T cell response that is reactive to the antigen and produce one or more of IFN-$\gamma$ and TNF-$\alpha$.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the immunogenic composition described herein to enhance the immunogenicity of the antigen.

"Antibody" as used herein means an antibody of classes IgG, IgM, IgA, IgD or IgE, or fragments, fragments or derivatives thereof, including Fab, F(ab')$_2$, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes, serotypes, or strains of a particular antigen. Synthetic antigens, such as fusion proteins, may be manipulated to generate consensus sequences (or consensus antigens).

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, the term "expressible form" refers to gene constructs that contain the necessary regulatory elements operably linked to a coding sequence that encodes a target protein or an immunomodulating protein, such that when present in the cell of the individual, the coding sequence will be expressed.

"Fragment" as used herein means a nucleotide sequence or a portion thereof that encodes a polypeptide capable of eliciting an immune response in a mammal. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full length endogenous antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a tumor microenvironment protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that is capable of being administered the immunogenic compositions described herein. The mammal can be, for example, a human, chimpanzee, dog, cat, horse, cow, mouse, or rat.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleotide sequence and a second nucleotide sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of a subject from a disease through means of preventing, suppressing, repressing, or completely eliminating the disease. In one embodiment, preventing the disease involves administering an immunogenic composition of the present invention to a subject prior to onset of the disease. In one embodiment, preventing the disease involves administering an immunogenic composition of the present invention to a subject following a treatment so as to prevent reoccurrence or further progression of the disease. Suppressing the disease involves administering an immunogenic composition of the present invention to a subject after induction of the disease but before its clinical appearance. Repressing the disease involves administering an immunogenic composition of the present invention to a subject after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleotide sequence that is substantially identical over the full length of the full gene sequence or a fragment thereof. The nucleotide sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Description

The invention provides an optimized consensus sequence encoding a FSHR antigen. In one embodiment, the FSHR antigen encoded by the optimized consensus sequence is capable of eliciting an immune response in a mammal. In one embodiment, the FSHR antigen encoded by the optimized consensus sequence can comprise an epitope(s) that makes it particularly effective as an immunogen against which an immune response can be induced.

The optimized consensus sequence can be a consensus sequence derived from two or more native FSHR proteins. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The FSHR antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The antigen encoded by the optimized consensus sequence can be designed to elicit stronger cellular and/or humoral immune responses than a corresponding native antigen. The antigen encoded by the optimized consensus sequence can be designed to break tolerance and synergize with anti-cancer immune therapy.

In one embodiment, an optimized consensus FSHR is designed to break tolerance to native human FSHR. In one embodiment, a human optimized consensus FSHR encoding sequence is as set forth in SEQ ID NO:1 or SEQ ID NO:3. In one embodiment, a human optimized consensus FSHR encoded antigen has an amino acid sequence as set forth in SEQ ID NO:2 or SEQ ID NO:4.

In one embodiment, an optimized consensus FSHR is designed to break tolerance to native mouse FSHR. In one embodiment, a mouse optimized consensus FSHR encoding sequence is as set forth in SEQ ID NO:5 or SEQ ID NO:7. In one embodiment, a mouse optimized consensus FSHR encoded antigen has an amino acid sequence as set forth in SEQ ID NO:6 or SEQ ID NO:8.

In one embodiment, an optimized consensus FSHR is designed to break tolerance to native canine FSHR. In one embodiment, a canine optimized consensus FSHR encoding sequence is as set forth in SEQ ID NO:9 or SEQ ID NO:11. In one embodiment, a canine optimized consensus FSHR encoded antigen has an amino acid sequence as set forth in SEQ ID NO:10 or SEQ ID NO:12.

In one embodiment, an optimized consensus encoded FSHR antigen is operably linked to one or more regulatory elements. In one embodiment, a regulatory element is a leader sequence. In one embodiment, the optimized consensus DNA sequence operably linked to an IgE leader encoding sequence is set forth in SEQ ID NO:3, SEQ ID NO:7 or SEQ ID NO:11. In one embodiment, the optimized consensus-encoded FSHR antigen operably linked to an IgE leader sequence is as set forth in SEQ ID NO:4, SEQ ID NO:8 or SEQ ID NO:12.

In one embodiment, a regulatory element is a start codon. Therefore, in one embodiment, the invention relates to a nucleic acid sequence as set forth in SEQ ID NO:1, SEQ ID NO:5 or SEQ ID NO:9, or a fragment or homolog thereof, operably linked to a nucleotide sequence comprising a start codon at the 5' terminus. In one embodiment, the invention relates to an amino acid sequence as set forth in SEQ ID NO:2, SEQ ID NO:6, or SEQ ID NO:10 or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleic acid sequence as set forth in SEQ ID NO:1, SEQ ID NO:3, SEQ ID NO:5, SEQ ID NO:7, SEQ ID NO:9 or SEQ ID NO:11 or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, the optimized consensus sequence encoding a FSHR antigen can encode a peptide having the amino acid sequence set forth in SEQ ID NO:2, SEQ ID NO:4, SEQ ID NO:6, SEQ ID NO:8, SEQ ID NO:10 or SEQ ID NO:12. In one embodiment, the optimized consensus sequence can have the nucleotide sequence set forth in SEQ ID NO:1, SEQ ID NO:3, SEQ ID NO:5, SEQ ID NO:7, SEQ ID NO:9 or SEQ ID NO:11. In some embodiments, the sequence can be the nucleotide sequence having at least about 96%, 97%, 98%, 99% or 100% identity over an entire length of the nucleotide sequence set forth in SEQ ID NO:1, SEQ ID NO:3, SEQ ID NO:5, SEQ ID NO:7, SEQ ID NO:9 or SEQ ID NO:11. In other embodiments, sequence can be the nucleotide sequence that encodes the amino acid sequence having at least about 96%, 97%, 98%, 99%, or 100% identity over an entire length of the amino acid sequence set forth in SEQ ID NO:2, SEQ ID NO:4, SEQ ID NO:6, SEQ ID NO:8, SEQ ID NO:10 or SEQ ID NO:12. In some embodiments, the optimized consensus FSHR antigen can be encoded by an RNA that is a transcript from a DNA sequence having at least about 96%, 97%, 98%, 99% or 100% identity over an entire length of the nucleic acid sequence set forth in the SEQ ID NO:1, SEQ ID NO:3, SEQ ID NO:5, SEQ ID NO:7, SEQ ID NO:9 or SEQ ID NO:11. In some embodiments, the optimized consensus FSHR antigen can be encoded by an RNA that encodes an amino acid sequence having at least about 96%, 97%, 98%, 99% or 100% identity over an entire length of the amino acid sequence set forth in SEQ ID NO:2, SEQ ID NO:4, SEQ ID NO:6, SEQ ID NO:8, SEQ ID NO:10 or SEQ ID NO:12.

The optimized consensus-encoded FSHR antigen can be a peptide having the amino acid sequence set forth in SEQ ID NO:2, SEQ ID NO:4, SEQ ID NO:6, SEQ ID NO:8, SEQ ID NO:10 or SEQ ID NO:12. In some embodiments, the antigen can have an amino acid sequence having at least about 96%, 97%, 98%, 99%, or 100% identity over an entire length of the amino acid sequence set forth in SEQ ID NO:2, SEQ ID NO:4, SEQ ID NO:6, SEQ ID NO:8, SEQ ID NO:10 or SEQ ID NO:12.

Immunogenic fragments of SEQ ID NO:2, SEQ ID NO:4, SEQ ID NO:6, SEQ ID NO:8, SEQ ID NO:10 or SEQ ID NO:12 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2, SEQ ID NO:4, SEQ ID NO:6, SEQ ID NO:8, SEQ ID NO:10 or SEQ ID NO:12. In some embodiments, immunogenic fragments include a leader sequence, such as for example an immunoglobulin leader, such as the IgE leader. In some embodiments, immunogenic fragments are free of a leader sequence.

In one embodiment, the nucleic acid sequence comprises an RNA sequence encoding a consensus FSHR immunogen sequence described herein. For example, nucleic acids may comprise an RNA sequence encoding one or more of SEQ ID NO:2, SEQ ID NO:4, SEQ ID NO:6, SEQ ID NO:8, SEQ ID NO:10 or SEQ ID NO:12, a variant thereof, a fragment thereof or any combination thereof.

Immunogenic fragments of proteins with amino acid sequences homologous to immunogenic fragments of SEQ ID NO:2, SEQ ID NO:4, SEQ ID NO:6, SEQ ID NO:8, SEQ ID NO:10 or SEQ ID NO:12 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4, SEQ ID NO:6, SEQ ID NO:8, SEQ ID NO:10 or SEQ ID NO:12. Some embodiments relate to immunogenic fragments that have 90% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO:1. Immunogenic fragments can be at least 60%, at least 65%, at least 70%, at least 75%, at least 80%, at least 85%, at least 90%, at least 95%, at least 96%, at least 97%, at least 98% or at least 99% of the full length of SEQ ID NO:1, SEQ ID NO:3, SEQ ID NO:5, SEQ ID NO:7, SEQ ID NO:9 or SEQ ID NO:11. Immunogenic fragments can be at least 96%, at least 97% at least 98% or at least 99% homologous to fragments of SEQ ID NO:1, SEQ ID NO:3, SEQ ID NO:5, SEQ ID NO:7, SEQ ID NO:9 or SEQ ID NO:11. In some embodiments, immunogenic fragments include sequences that encode a leader sequence, such as for example an immunoglobulin leader, such as the IgE leader. In some embodiments, fragments are free of coding sequences that encode a leader sequence.

Immunogenic Composition

Provided herein are immunogenic compositions, such as vaccines, comprising an optimized consensus sequence, an optimized consensus-encoded antigen, a fragment thereof, a variant thereof, or a combination thereof. The immunogenic composition can be used to reduce tumor growth or metastasis or protect against tumor development, thereby treating, preventing, and/or protecting against cancer based pathologies. The immunogenic composition can significantly induce an immune response of a subject administered with the immunogenic composition.

In one embodiment, the immunogenic composition can significantly induce an immune response of a subject administered with the immunogenic composition, thereby protecting against and treating cancer based pathologies in the subject.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

In one embodiment, immunogenic composition of the invention can be used to elicit protective anti-tumor immunity against, and prevent occurrence or recurrence of, e.g., ovarian cancer or other cancers characterized by tumor cells bearing the FSH receptor, e.g., prostate cancer cells and metastatic tumor lesions.

The vaccine can be an attenuated live vaccine, a vaccine using recombinant vectors to deliver antigen, subunit vaccines, and glycoprotein vaccines, for example, but not limited, the vaccines described in U.S. Pat. Nos.: 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,3 64; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose.

In one embodiment, the compositions and methods described herein are useful for treatment of cancer and tumor cells, i.e., both malignant and benign tumors, so long as the cells to be treated express FSHR. Thus, in various embodiments of the methods and compositions described herein, the cancer can include, without limitation, breast cancer, lung cancer, prostate cancer, colorectal cancer, esophageal cancer, stomach cancer, bladder cancer, pancreatic cancer, kidney cancer, cervical cancer, liver cancer, thyroid cancer, ovarian cancer, and testicular cancer.

In one embodiment, an immunogenic composition of the invention comprises a FSHR antigen and one or more additional cancer antigens.

Combinational Immunogenic Compositions for Treating Particular Cancers

The immunogenic composition can be in the form of various combinations of the antigen as described above with one or more cancer antigens to treat particular cancers or tumors. Depending upon the combination of one or more cancer antigens, various cancers or other tumor types may be targeted with the immunogenic composition. These cancers can include, but are not limited to ovarian cancer, prostate cancer, breast cancer, colon cancer, pancreatic cancer, urinary bladder cancer, kidney cancer, lung cancer, liver cancer, stomach cancer, and testicular cancer.

Cancer Antigens

The immunogenic composition can comprise one or more cancer antigens such as WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGSS, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen 1 to treat or prevent a tumor associated pathology. The immunogenic composition can further combine one or more cancer antigens WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGSS, SART3, STn, Carbonic anhydrase IX, PAX5, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen with an optimized consensus encoded FSHR antigen for treating or preventing a tumor associated pathology. Other combinations of cancer antigens may also be applied for treating or preventing a tumor associated pathology.

Ovarian Cancer Antigens

The immunogenic composition can comprise one or more cancer antigens such as CA-125, Beta human chorionic gonadotropin (beta-hCG), Urinary gonadotropin fragment, Alpha-fetoprotein (AFP), Inhibin, Carcinoembryonic antigen (CEA), Squamous cell carcinoma (SCC) antigen, Mullerian inhibiting substance (MIS), Topoisomerase II, Carbohydrate antigen 19-9, Cancer antigen 27-29, Human telomerase reverse transcriptase (hTERT) and Ferritin to treat or prevent ovarian cancer. The immunogenic composition can further combine one or more cancer antigens CA-125, Beta human chorionic gonadotropin (beta-hCG), Urinary gonadotropin fragment, Alpha-fetoprotein (AFP), Inhibin, Carcinoembryonic antigen (CEA), Squamous cell carcinoma (SCC) antigen, Müllerian inhibiting substance (MIS), Topoisomerase II, Carbohydrate antigen 19-9, Cancer antigen 27-29, Human telomerase reverse transcriptase (hTERT) and Ferritin with a FSHR antigen, for treating or preventing ovarian cancer. Other combinations of cancer antigens may also be applied for treating or preventing ovarian cancer.

Prostate Cancer Antigens

The immunogenic composition can comprise one or more cancer antigens such as PSA, PSMA, or STEAP to treat or prevent prostate cancer. The immunogenic composition can further combine one or more cancer antigens PSA, PSMA, or STEAP with a FSHA antigen for treating or preventing prostate cancer. Other combinations of cancer antigens may also be applied for treating or preventing prostate cancer. Exemplary PSA, PSMA, and STEP antigens, as well as nucleic acid molecules encoding such antigens, are disclosed in PCT application no. PCT/US11/60592 and corresponding U.S. Pat. No. 8,927,692, which are incorporated herein by reference.

Breast Cancer Antigens

The immunogenic composition can comprise one or more cancer antigens such as HER2, MUC-1, CEA, MAGE-3 and NY-ESO-1 to treat or prevent breast cancer. The immunogenic composition can further combine one or more cancer antigens HER2, MUC-1, CEA, MAGE-3 and NY-ESO-1 with a FSHA antigen for treating or preventing breast cancer. Other combinations of cancer antigens may also be applied for treating or preventing breast cancer.

Pancreatic Cancer Antigens

The immunogenic composition can comprise one or more cancer antigens such as MUC-1, CEA, HER2, Mesothelin, Survivin, and VEGFR2 to treat or prevent pancreatic cancer. The immunogenic composition can further combine one or more cancer antigens MUC-1, CEA, HER2, Mesothelin, Survivin, and VEGFR2 with a FSHA antigen for treating or preventing pancreatic cancer. Other combinations of cancer antigens may also be applied for treating or preventing pancreatic cancer.

Lung Cancer Antigens

The immunogenic composition can comprise one or more cancer antigens such as TERT, CD22, MAGE-3 and NY-ESO-1 to treat or prevent lung cancer. The immunogenic composition can further combine one or more cancer antigens TERT, CD22, MAGE-3 and NY-ESO-1 with a FSHA antigen for treating or preventing lung cancer. Other combinations of cancer antigens may also be applied for treating or preventing lung cancer.

Melanoma Antigens

The immunogenic composition can comprise one or more cancer antigens such as tyrosinase, PRAME, or GP100-Trp2 to treat or prevent melanoma.

The immunogenic composition can further combine one or more cancer antigen tyrosinase, PRAME, or GP100-Trp2 with a FSHA antigen for treating or preventing melanoma. Other combinations of cancer antigens may also be applied for treating or preventing melanoma.

Liver Cancer Antigens

The immunogenic composition can comprise one or more cancer antigens such as HBV core antigen, HBV surface antigen, HCVNS34A, HCVNS5A, HCV NS5B, or HCVNS4B to treat or prevent liver cancer. The immunogenic composition can further combine one or more cancer antigens HBV core antigen, HBV surface antigen, HCVNS34A, HCVNS5A, HCV NS5B, or HCVNS4B with a FSHA antigen for treating or preventing liver cancer. Other combinations of cancer antigens may also be applied for treating or preventing liver cancer.

Glioblastoma Antigens

The immunogenic composition can comprise CMV to treat or prevent glioblastoma. The immunogenic composition can further combine CMV with a FSHA antigen for treating or preventing glioblastoma. Other combinations of cancer antigens may also be applied for treating or preventing glioblastoma.

Blood Cancer Antigens (e.g., Leukemia, Lymphoma, Myeloma)

The immunogenic composition can comprise one or more cancer antigens such as PRAME, WT-1, hTERT to treat or prevent blood cancers such as leukemia, lymphoma and myeloma. The immunogenic composition can further combine one or more cancer antigens PRAME, WT-1, hTERT with a FSHA antigen for treating or preventing blood cancers such as leukemia, lymphoma and myeloma. Other combinations of cancer antigens may also be applied for treating or preventing blood cancers such as leukemia, lymphoma and myeloma cancer.

Immune Response

The immunogenic composition can induce an immune response in the subject administered the composition. The induced immune response can be specific for a native antigen. The induced immune response can be reactive with a native antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a native antigen. The induced humoral immune response can be reactive with the native antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized FSHR antigen.

The humoral immune response induced by the immunogenic composition can include an increased level of neutralizing antibodies associated with the subject administered the immunogenic composition as compared to a subject not administered the immunogenic composition. The neutralizing antibodies can be specific for a native antigen related to the optimized consensus-encoded antigen. The neutralizing antibodies can be reactive with the native antigen genetically related to the optimized consensus antigen. The neutralizing antibodies can provide protection against and/or treatment of tumor growth, metastasis or tumor associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the native antigen genetically related to the optimized consensus antigen. These IgG antibodies can be reactive with the native antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized FSHR antigen.

The immunogenic composition can induce a cellular immune response in the subject administered the immunogenic composition. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a CD8$^+$ T cell response. The elicited CD8$^+$ T cell response can be reactive with the native antigen genetically related to the optimized consensus antigen. The elicited CD8$^+$ T cell response can be polyfunctional. The induced cellular immune response can include eliciting a CD8$^+$ T cell response, in which the CD8$^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased CD8$^+$ T cell response associated with the subject administered the immunogenic composition as compared to the subject not administered the immunogenic composition. The CD8$^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8$^+$ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized FSHR antigen.

The induced cellular immune response can include an increased frequency of CD107a/IFN$\gamma$/T-bet triple-positive CD8 T cells that are reactive against the native antigen. The frequency of CD107a/IFN$\gamma$/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized FSHR antigen.

The induced cellular immune response can include an increased frequency of CD107a/IFN$\gamma$ double-positive CD8 T cells that are reactive against the native antigen. The frequency of CD107a/IFN$\gamma$ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized FSHR antigen.

The cellular immune response induced by the immunogenic composition can include eliciting a CD4$^+$ T cell response. The elicited CD4$^+$ T cell response can be reactive with the native antigen genetically related to the optimized consensus antigen. The elicited CD4$^+$ T cell response can be polyfunctional. The induced cellular immune response can include eliciting a CD4$^+$ T cell response, in which the CD4$^+$ T cells produce IFN-$\gamma$, TNF-$\alpha$, IL-2, or a combination of IFN-$\gamma$ and TNF-$\alpha$.

The induced cellular immune response can include an increased frequency of CD4$^+$ T cells that produce IFN-$\gamma$. The frequency of CD4$^+$IFN-$\gamma^+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized FSHR antigen.

The induced cellular immune response can include an increased frequency of CD4$^+$ T cells that produce TNF-$\alpha$. The frequency of CD4$^+$TNF-$\alpha^+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized FSHR antigen.

The induced cellular immune response can include an increased frequency of CD4$^+$ T cells that produce both IFN-$\gamma$ and TNF-$\alpha$. The frequency of CD4$^+$ IFN-$\gamma^+$TNF-$\alpha^+$ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized FSHR antigen.

The immunogenic composition of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic composition can further induce an immune response when administered to different tissues such as the muscle or skin. The immunogenic composition can further induce an immune response when administered via electroporation, or injection, or subcutaneously, or intramuscularly.

Fragments

In one embodiment, the immunogenic fragment is an immunogenic fragment of a full length antigen of the invention. As used herein, an immunogenic fragment is a fragment of a full length nucleic acid or amino acid sequence that can induce an immune response significantly similar to that of the full length sequence. In one embodiment, an immunogenic fragment comprises an immunogenic epitope of a full length sequence. In one embodiment, the immunogenic fragment induces an immune response at least about 0.7-fold, at least about 0.8-fold, at least about 0.9-fold, at least about 1.0-fold, at least about 1.1-fold, at least about 1.2-fold, at least about 1.3-fold, at least about 1.4-fold, at least about 1.5-fold, at least about 2.0-fold or greater than 2.0-fold as compared to the full length sequence.

The immunogenic fragment can induce a humoral immune response in the subject administered the immunogenic fragment. The humoral immune response can be induced in the subject administered the immunogenic fragment by about 1.5-fold to about 16-fold, about 2-fold to about 12-fold, or about 3-fold to about 10-fold. The humoral immune response can be induced in the subject administered the immunogenic fragment by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered immunogenic fragment.

The humoral immune response induced by the immunogenic fragment can include an increased level of IgG antibodies associated with the subject administered the immunogenic fragment as compared to a subject not administered the immunogenic fragment. The level of IgG antibody associated with the subject administered the immunogenic fragment can be increased by about 1.5-fold to about 16-fold, about 2-fold to about 12-fold, or about 3-fold to about 10-fold as compared to the subject not administered the immunogenic fragment. The level of IgG antibody associated with the subject administered the immunogenic fragment can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic fragment.

The immunogenic fragment can induce a cellular immune response in the subject administered the immunogenic fragment. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a $CD8^+$ T cell response. The elicited $CD8^+$ T cell response can be reactive with the native antigen genetically related to the optimized consensus antigen. The elicited $CD8^+$ T cell response can be polyfunctional. The induced cellular immune response can include eliciting a $CD8^+$ T cell response, in which the $CD8^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased $CD8^+$ T cell response associated with the subject administered the immunogenic fragment as compared to the subject not administered the immunogenic fragment. The $CD8^+$ T cell response associated with the subject administered the immunogenic fragment can be increased by about 2-fold to about 30-fold, about 3-fold to about 25-fold, or about 4-fold to about 20-fold as compared to the subject not administered the immunogenic fragment. The $CD8^+$ T cell response associated with the subject administered the immunogenic fragment can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic fragment.

The induced cellular immune response can include an increased frequency of CD107a/IFN$\gamma$/T-bet triple-positive CD8 T cells that are reactive against the native antigen. The frequency of CD107a/IFN$\gamma$/T-bet triple-positive CD8 T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic fragment.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic.

The cellular immune response induced by the immunogenic fragment can include eliciting a CD4$^+$ T cell response. The elicited CD4$^+$ T cell response can be reactive with the native antigen genetically related to the optimized consensus antigen. The elicited CD4$^+$ T cell response can be polyfunctional. The induced cellular immune response can include eliciting a CD4$^+$ T cell response, in which the CD4$^+$ T cells produce IFN-γ, TNF-α, IL-2, or a combination of IFN-γ and TNF-α.

The induced cellular immune response can include an increased frequency of CD4$^+$ T cells that produce IFN-γ. The frequency of CD4$^+$IFN-γ$^+$ T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic fragment.

The induced cellular immune response can include an increased frequency of CD4$^+$ T cells that produce TNF-α. The frequency of CD4$^+$TNF-α$^+$ T cells associated with the subject administered the immunogenic fragment can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic fragment.

The induced cellular immune response can include an increased frequency of CD4$^+$ T cells that produce both IFN-γ and TNF-α. The frequency of CD4$^+$IFN-γ$^+$TNF-α$^+$ associated with the subject administered the immunogenic fragment can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic fragment.

The immunogenic fragment of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic fragment can further induce an immune response when administered to different tissues such as the muscle or skin. The immunogenic fragment can further induce an immune response when administered via electroporation, or injection, or subcutaneously, or intramuscularly.

Vector

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) RNA Vectors

In one embodiment, the nucleic acid is an RNA molecule. Accordingly, in one embodiment, the invention provides an RNA molecule encoding one or more MAYV antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(3) Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid immunogenic composition, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleotide sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be pcrM2. The LEC can be pcrNP. pcrNP and pcrMR can be derived from pNP (Puerto Rico/34) and pM2 (New Caledonia/99), respectively.

(4) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleotide sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Multiple Vectors

The immunogenic composition may comprise a plurality of copies of a single nucleic acid molecule such a single plasmid, or a plurality of copies of two or more different nucleic acid molecules such as two or more different plasmids. For example an immunogenic composition may comprise plurality of two, three, four, five, six, seven, eight, nine or ten or more different nucleic acid molecules. Such compositions may comprise plurality of two, three, four, five, six, or more different plasmids.

Immunogenic compositions may comprise nucleic acid molecules, such as plasmids, that collectively contain coding sequence for a FSHR antigen. Immunogenic compositions may comprise nucleic acid molecules, such as plasmids, that collectively contain coding sequence for multiple antigens. In one embodiment, the antigens are a FSHR antigen and one or more additional cancer antigen. Immunogenic compositions may comprise nucleic acid molecules, such as plasmids, that collectively contain coding sequence for one or more antigen and one or more cancer antigen.

Excipients and other Components of the Immunogenic Composition

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid-based immunogenic compositions may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-18, IL-23, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof, or a combination thereof. In some embodiments adjuvant may be one or more proteins and/or nucleic acid molecules that encode proteins selected from the group consisting of: RANTES, IL-12, IL-15, IL-23, IL-28, CTACK, TECK, MEC, OX40 and DRS. Examples of IL-12 constructs and sequences are disclosed in PCT application no. PCT/US12/69017 and corresponding U.S. Pat. No. 9,272,024, which are incorporated herein by reference. Examples of IL-15 constructs and sequences are disclosed in PCT application no. PCT/US04/18962 and corresponding U.S. Pat. No. 8,173,786, which are each incorporated herein by reference. Examples of IL-23 constructs and sequences are disclosed in PCT application no. PCT/US14/25348 and corresponding U.S. application Ser. No. 14/775,087, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. Pat. No. 8,119,395, which are each incorporated herein by reference. Other examples of RANTES constructs and sequences are disclosed in PCT application no. PCT/US11/024098 and corresponding U.S. Pat. No. 9,034,313, which are incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DRS and other immunomodulators are disclosed in U.S. application Ser. No. 09/622,452, which is incorporated herein by reference.

The immunogenic composition may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95,100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95,100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The immunogenic composition may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. An immunogenic composition may further comprise stabilizers including gelatin and albumin. The stabilizing may allow the formulation to be stable at room or ambient temperature for extended periods of time such as LGS or polycations or polyanions to the vaccine formulation.

The immunogenic composition may be stable for is stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the immunogenic composition is stable under refrigeration (2-8° C.). Accordingly, in one embodiment, the immunogenic composition does not require frozen cold-chain. An immunogenic composition is stable if it retains its biological activity for a sufficient period to allow its intended use (e.g., to generate an immune response in a subject). For example, for immunogenic compositions that are to be stored, shipped, etc., it may be desired that the immunogenic compositions remain stable for months to years.

Method of Vaccination

Also provided herein is a method of treating, protecting against, and/or preventing disease in a subject in need thereof by administering the immunogenic composition to the subject. Administration of the immunogenic composition to the subject can induce or elicit an immune response in the subject. The induced immune response can be used to treat, prevent, and/or protect against disease, for example, one or more tumor associated pathologies.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced humoral immune response can include IgG antibodies and/or neutralizing antibodies that are reactive to the antigen. The induced cellular immune response can include a $CD8^+$ T cell response, which is induced by about 2-fold to about 30-fold, about 3-fold to about25-fold, or about 4-fold to about 20-fold.

The immunogenic composition dose can be between 1 μg to 10 mg active component/kg body weight/time, and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the DNA of the immunogenic composition in particular, the immunogenic composition can be delivered to the interstitial spaces of tissues of an individual (Feigner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Feigner et al., U.S. Pat. No. 5,703,055; Gregoriadis, Liposome Technology, Vols. Ito III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The immunogenic composition can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the immunogenic composition described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the immunogenic composition into tissue without the use of a needle. The MID may inject the immunogenic composition as a small stream or jet with such force that the immunogenic composition pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired immunogenic composition in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the immunogenic composition into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver immunogenic compositions to all types of tissues, particularly to skin and mucosa. In some embodiments, a needle-free injector may be used to propel a liquid that contains the immunogenic composition to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle immunogenic composition injectors that deliver the immunogenic composition and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell PA) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described immunogenic composition herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

Generation of Antigens In Vitro and Ex Vivo

In one embodiment, the optimized consensus FSHR antigen is generated in vitro or ex vivo. For example, in one embodiment, a nucleic acid encoding an optimized consensus FSHR antigen can be introduced and expressed in an in vitro or ex vivo cell.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Method of Preparing DNA Plasmids

Provided herein is methods for preparing the DNA plasmids that comprise the DNA based immunogenic compositions discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Method of Treatment

The immunogenic composition can be used to generate or elicit an immune response in a mammal that is reactive or directed to FSHR of a subject in need thereof. In one embodiment the immunogenic composition can be used to prevent or treat a cancer in the subject. In one embodiment, the cancer expresses FSHR. Accordingly, the immunogenic composition can be used in a method that treats and/or prevents an FSHR expressing cancer in the subject administered the immunogenic composition. In one embodiment, the immunogenic composition can be used to prevent a primary or initial occurrence of an FSHR expressing cancer in a subject. In one embodiment, the immunogenic composition can be used to prevent recurrence of an FSHR expressing cancer in a subject.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the immunogenic composition.

In some embodiments, the administered immunogenic composition can increase survival of cancer, reduce tumor size, or a combination thereof in the subject. The administered immunogenic composition can increase survival of cancer by 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject. The administered immunogenic composition can reduce tumor size by 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject after immunization.

The administered immunogenic composition can increase a cellular immune response in the subject by about 5-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered immunogenic composition can increase the cellular immune response in the subject by about 5-fold, 10-fold, 20-fold, 30-fold, 40-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-γ) levels in the subject by about 5-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 μg to 10 mg active component/kg body weight/time and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Routes of Administration

The immunogenic or pharmaceutical composition can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administering to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The optimized consensus FSHR antigen of the invention can be administered via DNA injection along with in vivo electroporation.

Kit

Provided herein is a kit, which can be used for treating a subject using the method of vaccination described above. The kit can comprise the immunogenic composition.

The kit can also comprise instructions for carrying out the vaccination method described above and/or how to use the kit. Instructions included in the kit can be affixed to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an interne site which provides instructions.

The present invention has multiple aspects, illustrated by the following non-limiting examples.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Optimized Consensus FSHR Immunogenic Composition

DNA vaccines have potent anti-tumor activity in humans. Synthetic consensus DNA vaccines have been designed to break tolerance and redirect the immune system towards the FSHR protein. DNA vaccines based on consensus sequences have shown promise in the clinic, accomplishing the clearance of cervical intraepithelial neoplasia. An advantage of this approach over peptide vaccines is that it can elicit an immune response against multiple peptides derived from the endogenous natural cleavage of the protein and be presented in all the different variants of MHC class I and II.

DNA cancer vaccines have proved successful against tumors with viral antigens, however, this success has not been yet translated into effective responses against aggressive and frequent cancers such as ovarian carcinomas. One of the limitations has been the lack of targetable antigens selectively expressed by tumor cells and not by healthy tissues, which could result in fatal adverse effects. The optimized consensus sequence described herein has been designed to elicit an immune response against FSHR, a targetable antigen present in 50-70% of ovarian carcinoma (FIG. 1).

Priming through optimized consensus FSHR DNA vaccine enhances the number of T-cells targeting FSHR+ tumor cells and increases the amount of tumor infiltrating T-cells. In addition, combinatorial targeting of suppressive networks operating in the ovarian cancer microenvironment unleashes tumor-infiltrating lymphocytes from tolerogenic pathways that could dampen their protective activity, thus addressing a known limitation of the activity of T-cells in solid tumors.

The methods are now described.

Optimized Consensus FSHR DNA Vaccine

Figure 2:
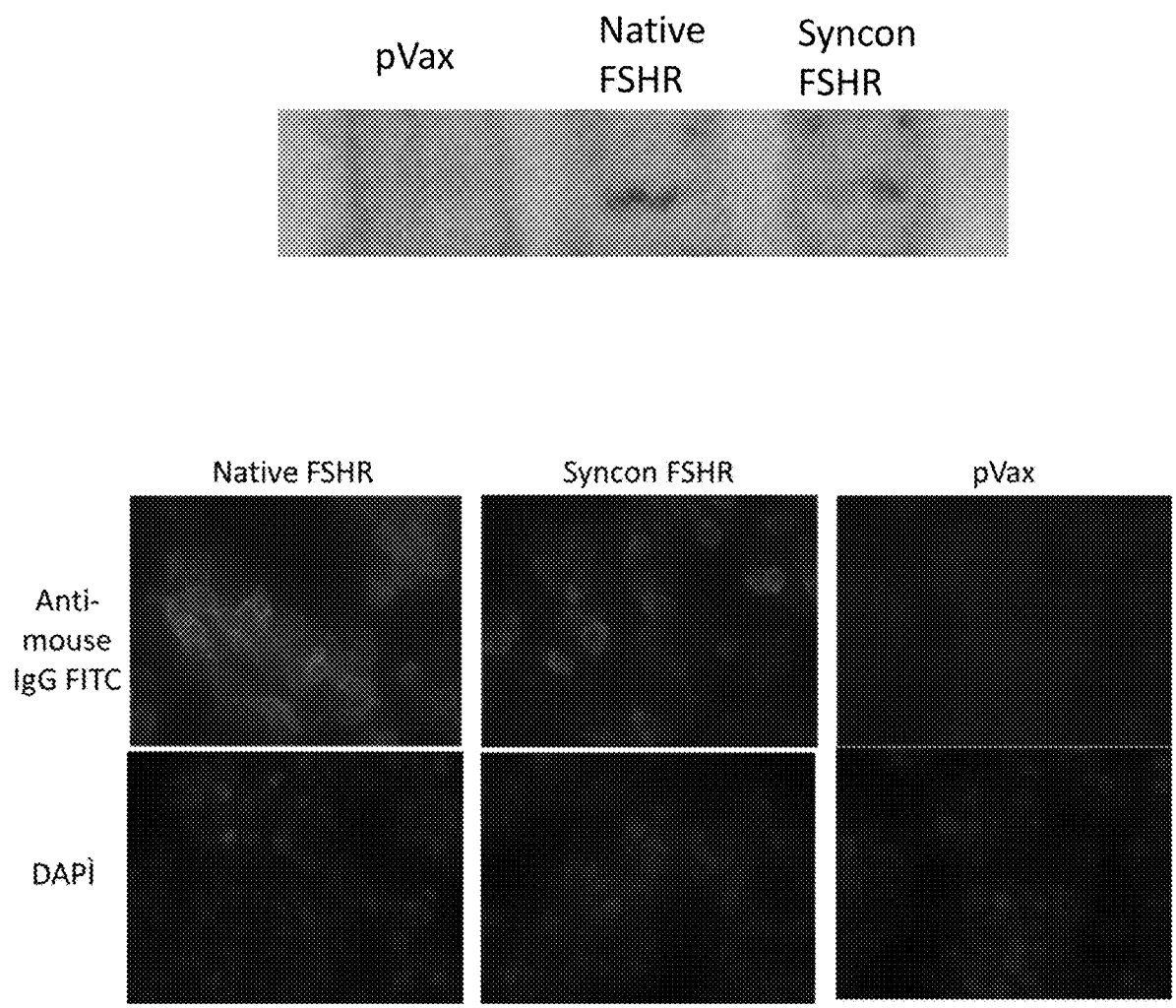
FIG. 2 depicts exemplary experimental results demonstrating that the consensus FSHR vaccine expresses in vitro.

An optimized consensus DNA vaccine targeting FSHR has been developed. A consensus FSHR was generated by using 55 FSHR sequences collected from GenBank. Mutations essential for hormone activity and G-protein activation were introduced. The optimized FSHR DNA has been designed to include the following features: RNA changes to improve ribosome loading, mRNA stability, increased GC content; codon usage refocused for improved translation; very high and very low GC regions minimized; cis-acting motifs, repeat sequences, instability sequences, and RNA structure motifs removed; efficient Kozak sequence introduced; IgE leader sequence added; and mutations incorporated to inactivate receptor activity and break tolerance. Expression of the optimized consensus FSHR is shown in FIG. 2.

Five mice per group provides a 5% significance level and 95% power to detect differences of 20% or greater, using Mann-Whitney's or Wilcoxon's tests. Unless otherwise stated, experiments use at least 5 mice/group (plus a repetition) and are analyzed according to these statistical parameters.

Figure 3A:
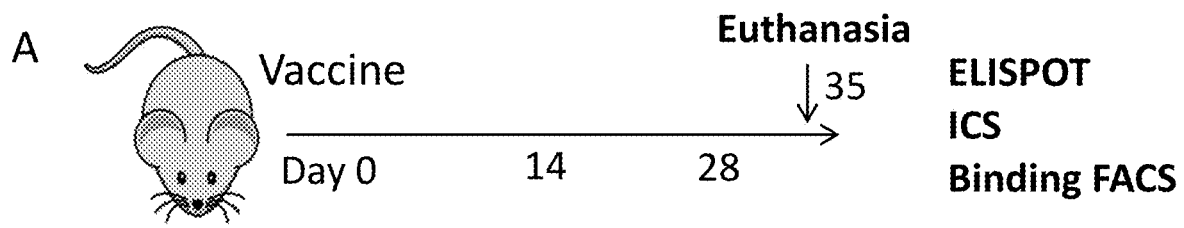
FIG. 3A through FIG. 3C, depicts exemplary experimental results demonstrating that FSHR vaccines generate a strong IFNg response.

Vaccinations of mice are performed by injection of approximately 20 ug of DNA into the tibialis anterior muscle followed by electroporation with CELLECTRA device. Naïve mice are vaccinated with mouse optimized consensus FSHR three times at two-week intervals. Control mice receive native mouse FSHR or empty pVax vector. The mice are sacrificed one week after the last vaccination in order to examine the humoral and cellular immune responses (FIG. 3A). To determine humoral response, enzyme-linked immunosorbent assay (ELISA) against recombinant FHSR protein is used to measure the titer of anti-FSHR antibodies in mouse sera. To determine the cellular response, isolated splenocytes are stimulated with murine FSHR protein, and mouse IFNγ and Granzyme B enzyme-linked immunosorbent spot (ELISpot) assays are perfomed with staining for CD107a, IFNγ, TNFα, CD4OL, CD44, CD69 and CD62L. The frequencies of effector memory (CD44+/CD62L-) and central memory (CD44int-hi/CD62Lhi) CD8 T cells are examined. Finally, the frequency of suppressor regulatory T-cells (CD4+CD25+FoxP3+ Tregs) is examined. The cytolytic CD8+ response is evaluated using an in vivo cytotoxicity assay. Briefly, splenocytes are isolated from congenic (CD45.1+) naïve mice, stained with either high or low dose of carboxyfluorescein diacetate succinimidyl ester (CFSE), and loaded with relevant (FSHR) or irrelevant peptides. These cells are then be injected into either naïve or immunized mice for 48 hours, isolated again and the frequencies measured by flow cytometry. The percentage killing can be calculated based on the remaining frequency of CFSEhi and CFSElo populations.

The results are now described

Consensus FSHR Immunization Induces a Potent IFN Gamma Response

Figure 3B:
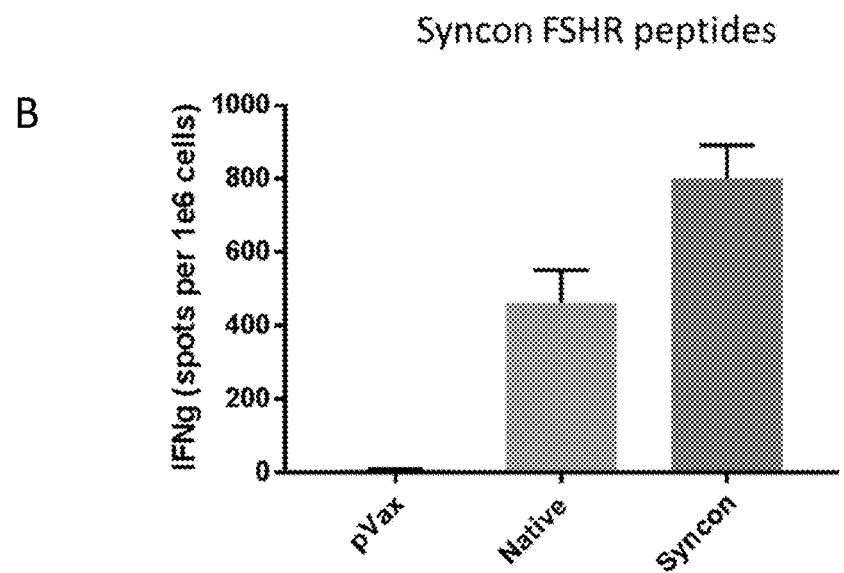
Figure 3C:
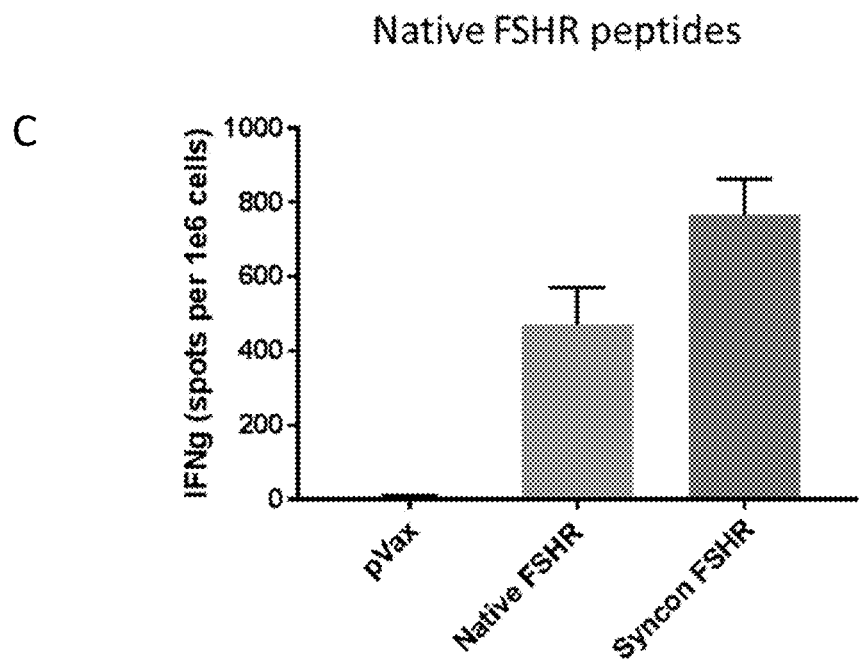
Figure 4:
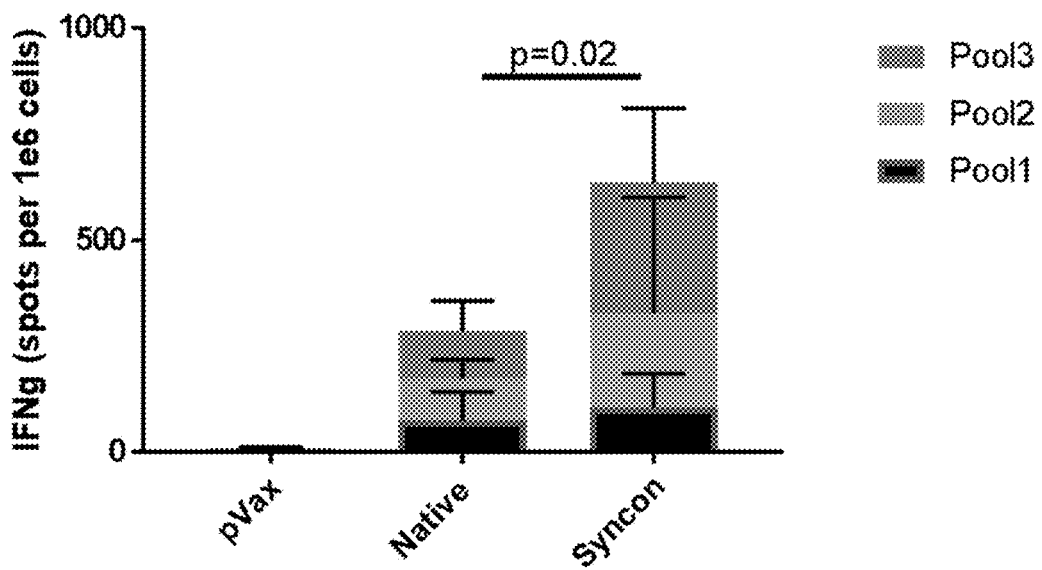
FIG. 4 depicts exemplary experimental results demonstrating that the IFNγ responses induced by syncon FSHR are primarily against peptide pool 2 (overlapping part of the FSH binding domain and part of the transmembrane domain) and peptide pool 3 (overlapping part of the transmembrane domain and the intracellular domain).
Figure 4:
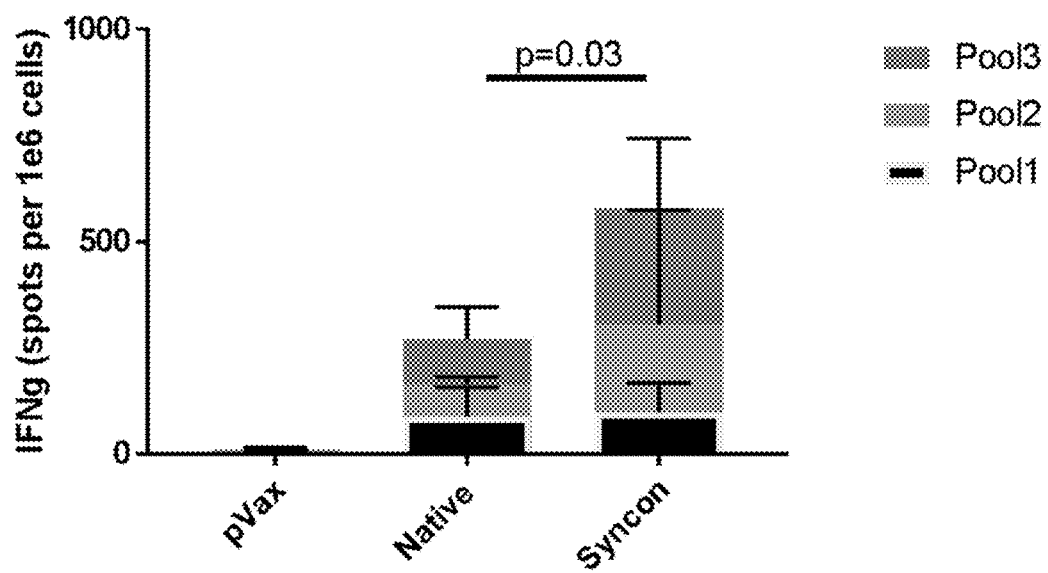
Figure 5:
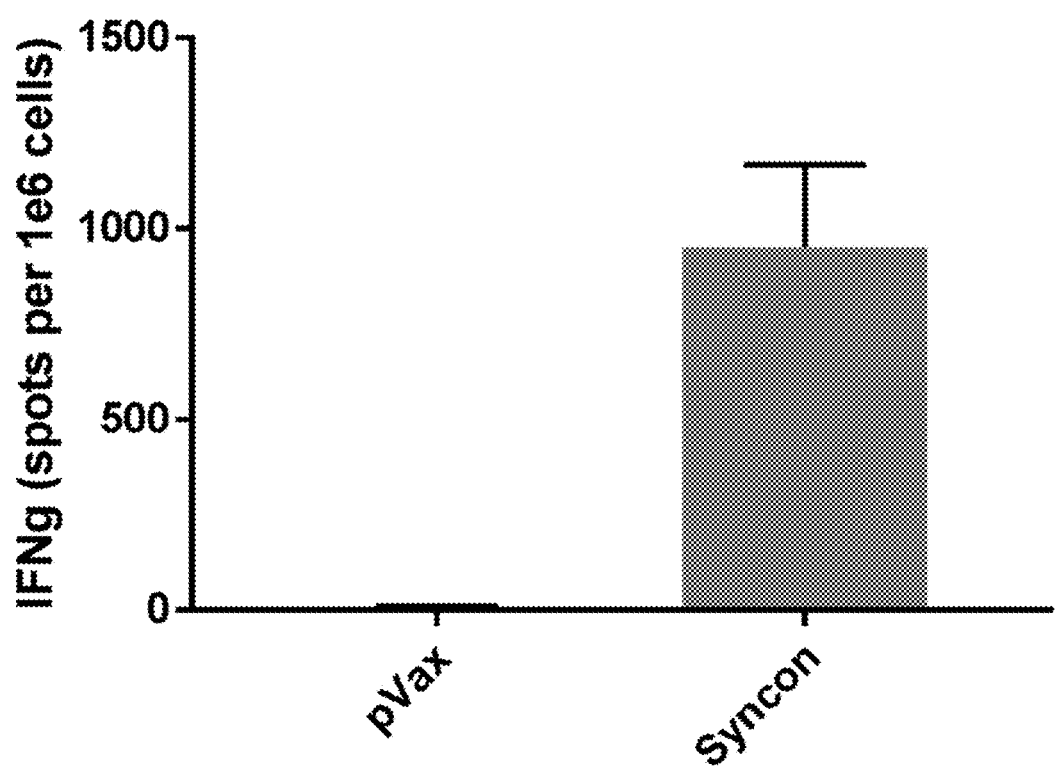
FIG. 5 depicts exemplary experimental results demonstrating that immunization with the consensus FSHR DNA vaccine breaks tolerance against FSHR and induces a potent IFN gamma response.
Figure 6:
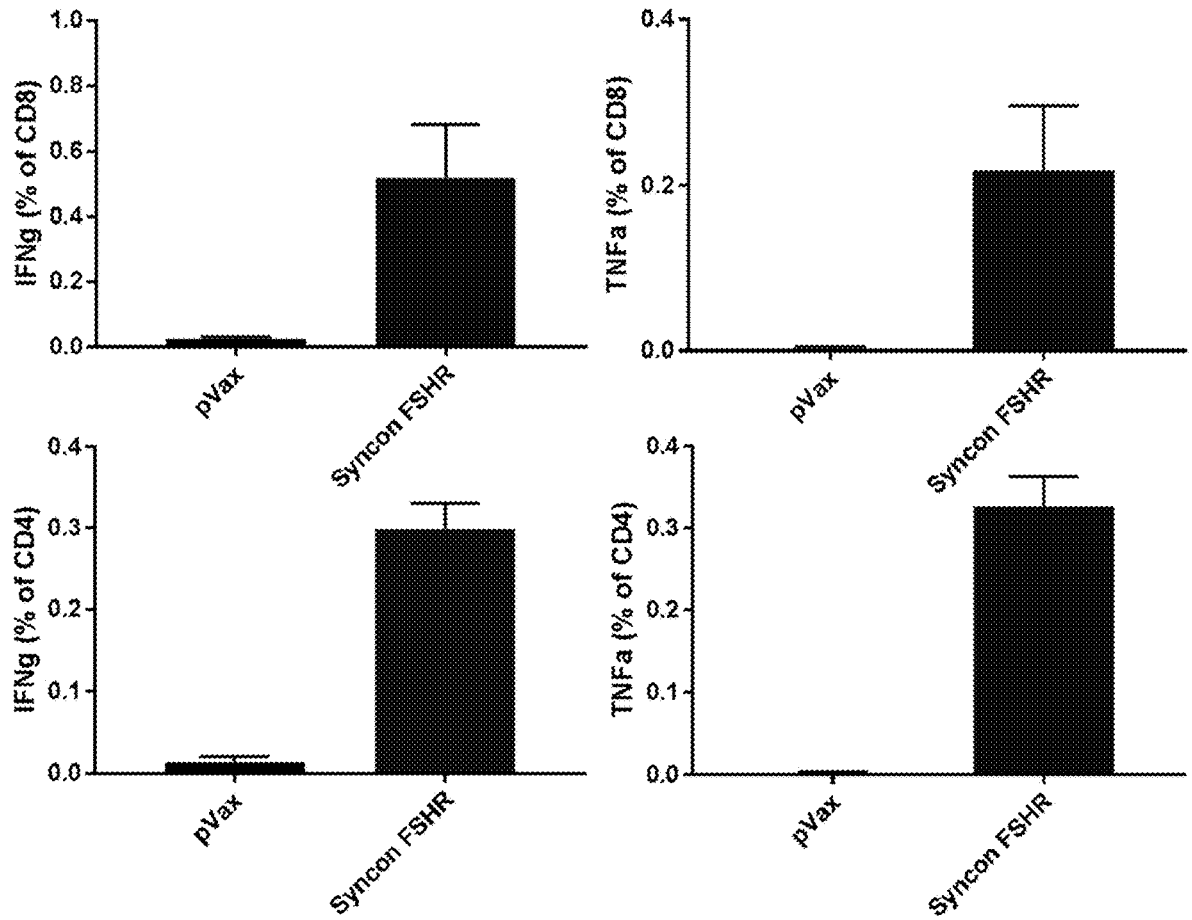
FIG. 6 depicts exemplary experimental results demonstrating that immunization with the consensus FSHR DNA vaccine induces a strong CD8 and CD4 T cell response.

To determine if the mouse consensus FSHR DNA vaccine was able to break tolerance against native FSHR, naïve mice were immunized mice with 3 doses of FSHR DNA vaccine in 2 week intervals and sacrificed a week after the last immunization. Interferon-γ ELISPOT was performed with splenocytes derived from the immunized mice pulsed with peptides derived from murine FSHR. A strong cellular response was observed against the peptides derived from the vaccine protein when compared with the pVax treated mice (FIG. 3 through FIG. 5).

Consensus FSHR Immunization Induces a Strong CD8 and CD4 T cell response

Figure 7:
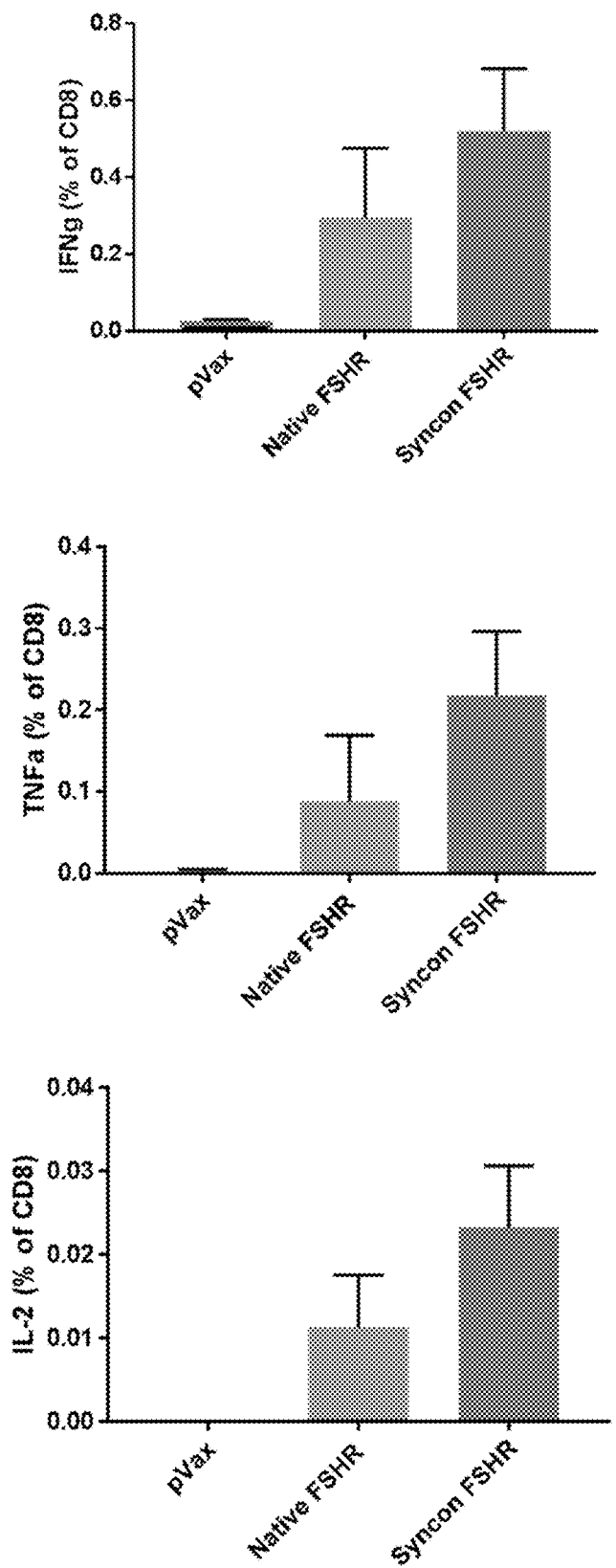
FIG. 7 depicts exemplary experimental results demonstrating that immunization with the consensus FSHR DNA vaccine induces a stronger CD8 T cell response than immunization with native FSHR.
Figure 8:
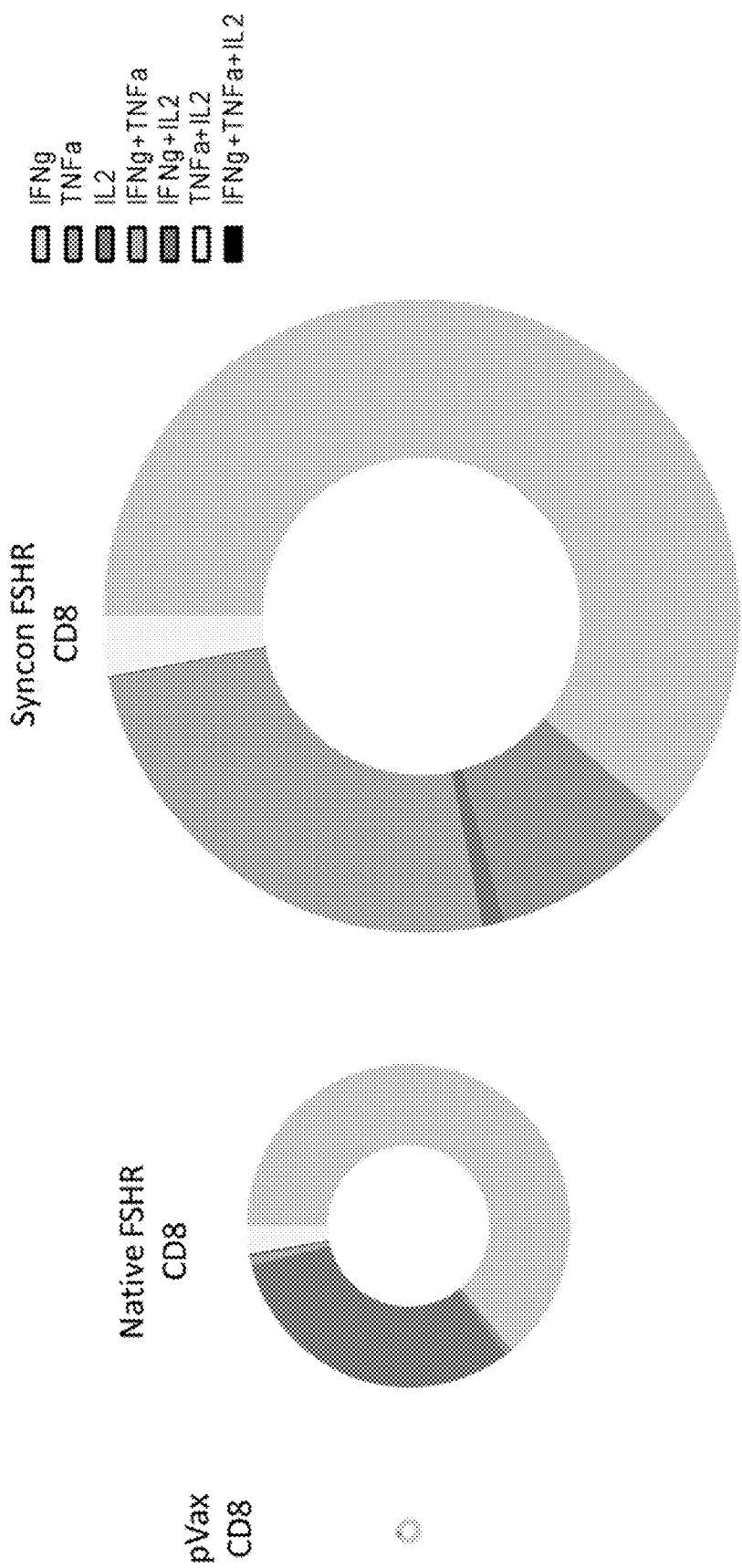
FIG. 8 depicts exemplary experimental results demonstrating that immunization with the consensus FSHR DNA vaccine elicits a significant CD8 response, including a greater percentage of TNFα CD8 T cells than immunization with the native FSHR sequence.
Figure 9:
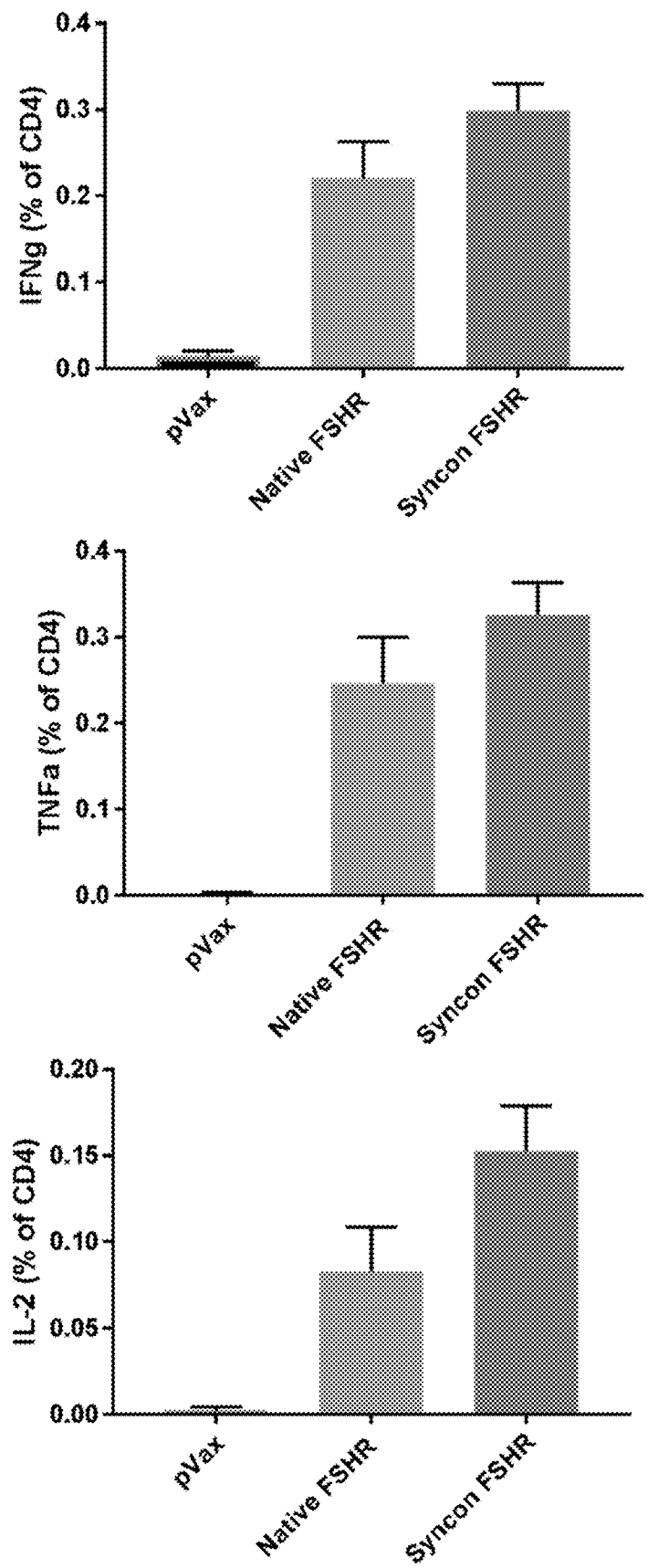
FIG. 9 depicts exemplary experimental results demonstrating that immunization with the consensus FSHR DNA vaccine induces a stronger CD4 Th1 response than immunization with native FSHR.
Figure 10:
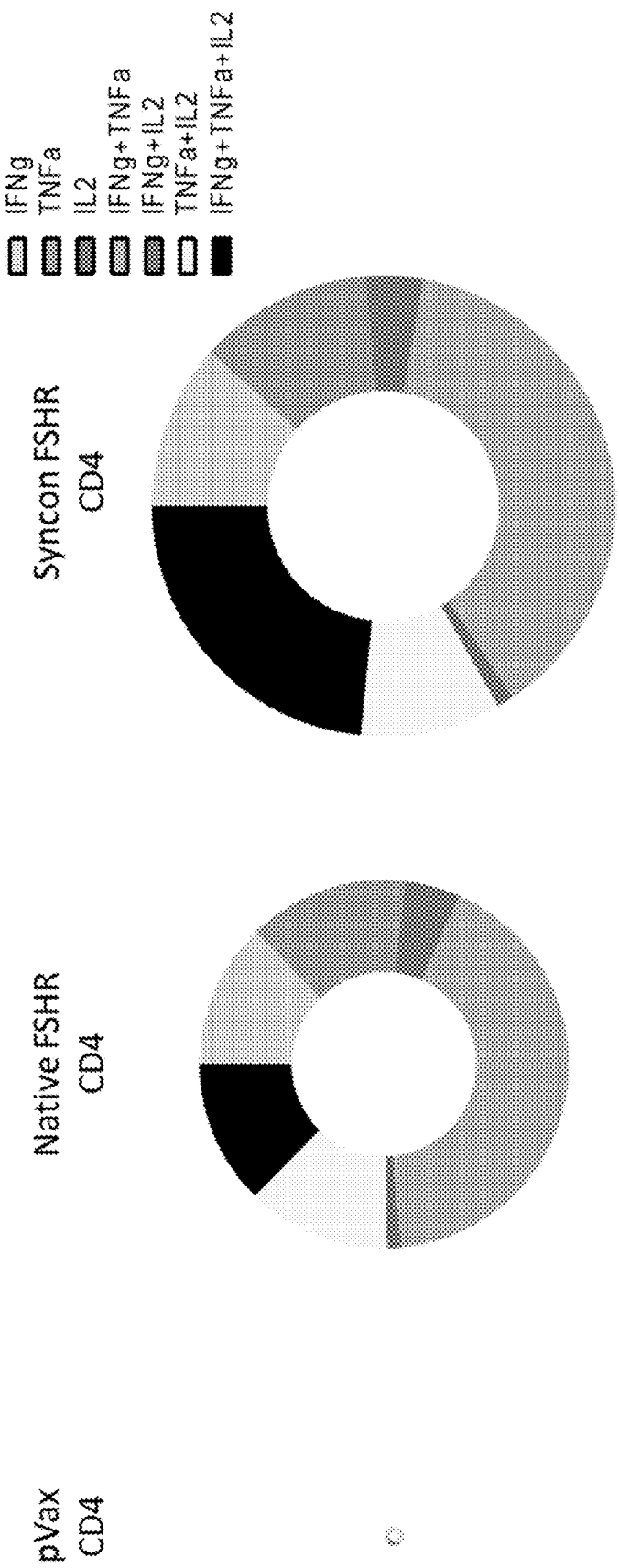
FIG. 10 depicts exemplary experimental results demonstrating that immunization with the consensus FSHR DNA vaccine elicits a significant CD4 Th1 response, including a greater percentage of IFNγ/TNFα/IL2 CD4 T cells than immunization with the native FSHR sequence.

To determine what specific cell types were responsible for the IFNg induction, intracellular flow cytometry was performed with FSHR peptide pulsed splenocytes. Both CD4 and CD8 T-cells were being stimulated by the mouse consensus FSHR vaccine (FIG. 6 through FIG. 10). Not only was there increased IFNγ production, but also increased production of TNFα (FIG. 7 and FIG. 8).

Vaccine Adjuvants Increase the Immune Response of the Consensus FSHR Vaccine Against FSHR The number of dendritic cells present at the site of vaccination has been shown to be a limiting factor in the ability of vaccines to elicit an effective immune response (Kutzler and Weiner, J Clin Invest. 2004, 114:1241-1244). Different adjuvants injected simultaneously with the DNA vaccines are able to increase its immunogenicity (Villarreal et al., Mol Ther. 2015, 23:1653-1662; Villarreal et al., Vaccine, 2015, 33:4313-4320; Villarreal et al., Cancer Res. 2014, 74:1789-1800) and skew the immune responses towards a Th1 or Th2 response according to the specific needs. Different adjuvants co-transfected (IL-124,11,15, GM-CSF15,21 and IL-15/IL-15Ra10,13,14) together with the optimized consensus FSHR DNA vaccine shows an increased cellular immune response, and a more effective anti-tumor effect in its clinical application.

Figure 11:
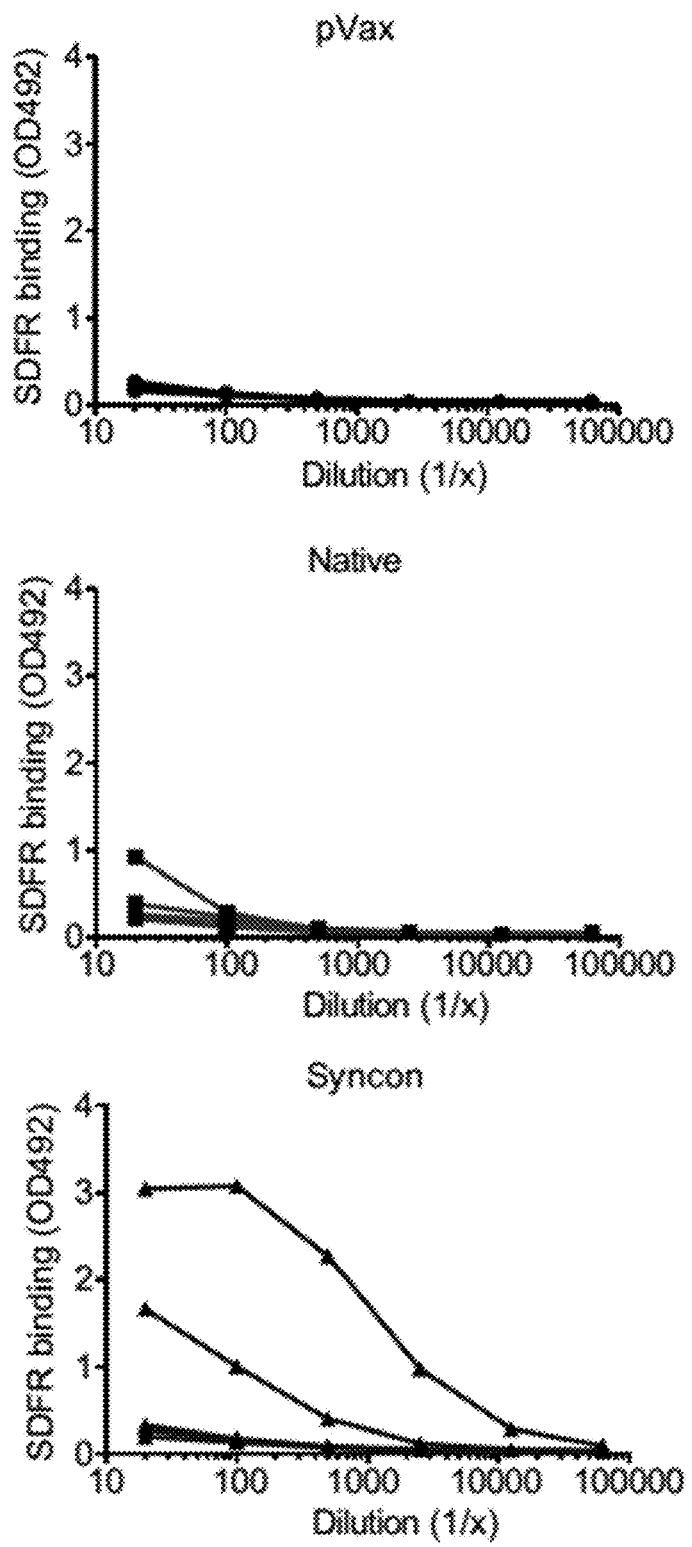
FIG. 11 depicts exemplary experimental results demonstrating that the FSHR vaccine generates antibody responses.
Figure 12A:
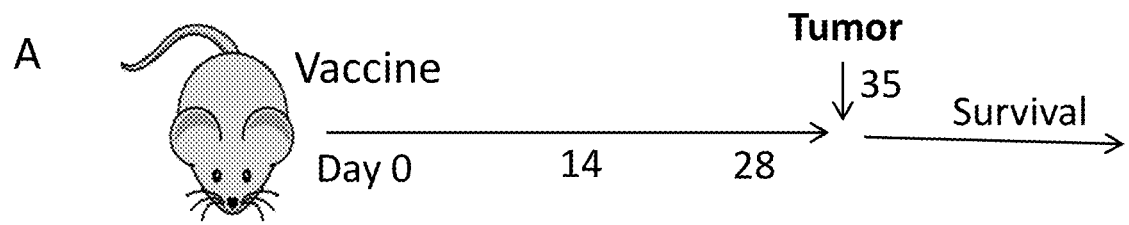
FIG. 12A through FIG. 12C, depicts exemplary experimental results demonstrating that the FSHR vaccine is able to delay tumor progression in a prophylactic manner.
Figure 12B:
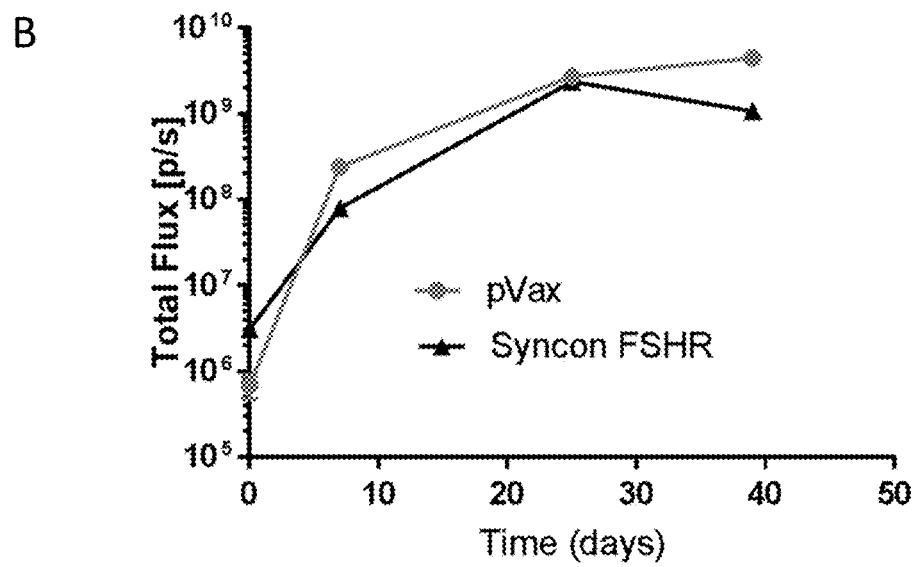
Figure 12C:
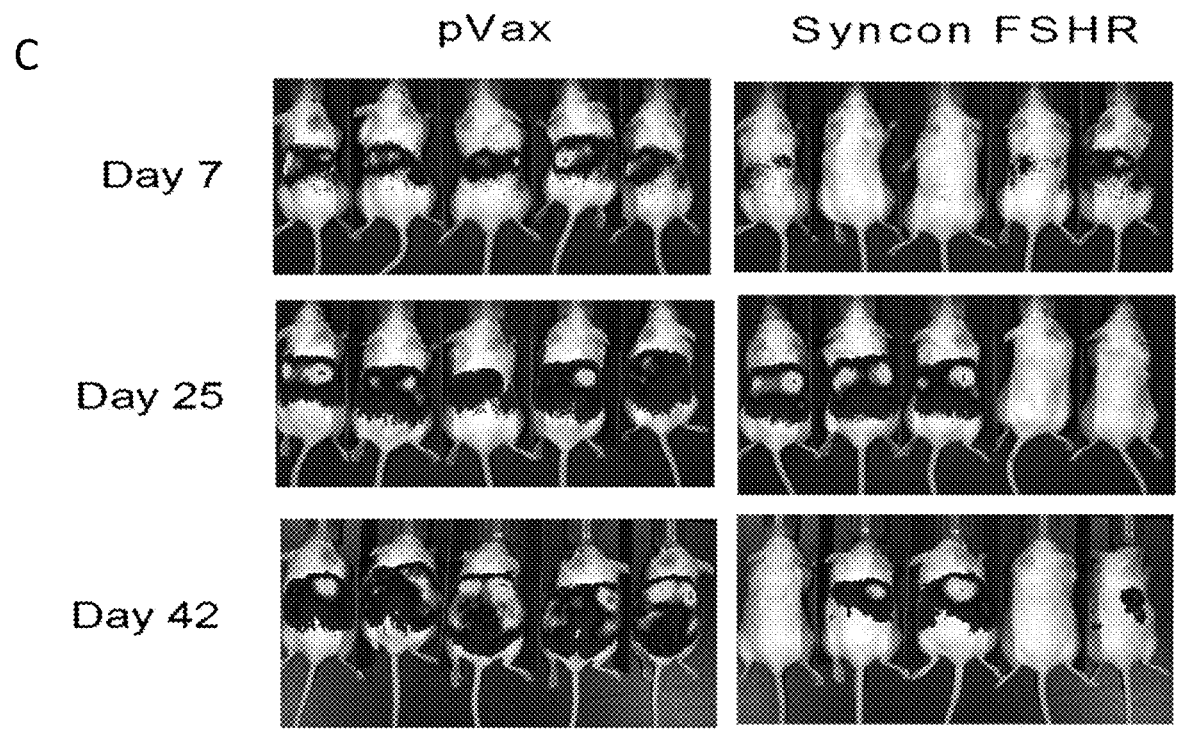
Figure 13:
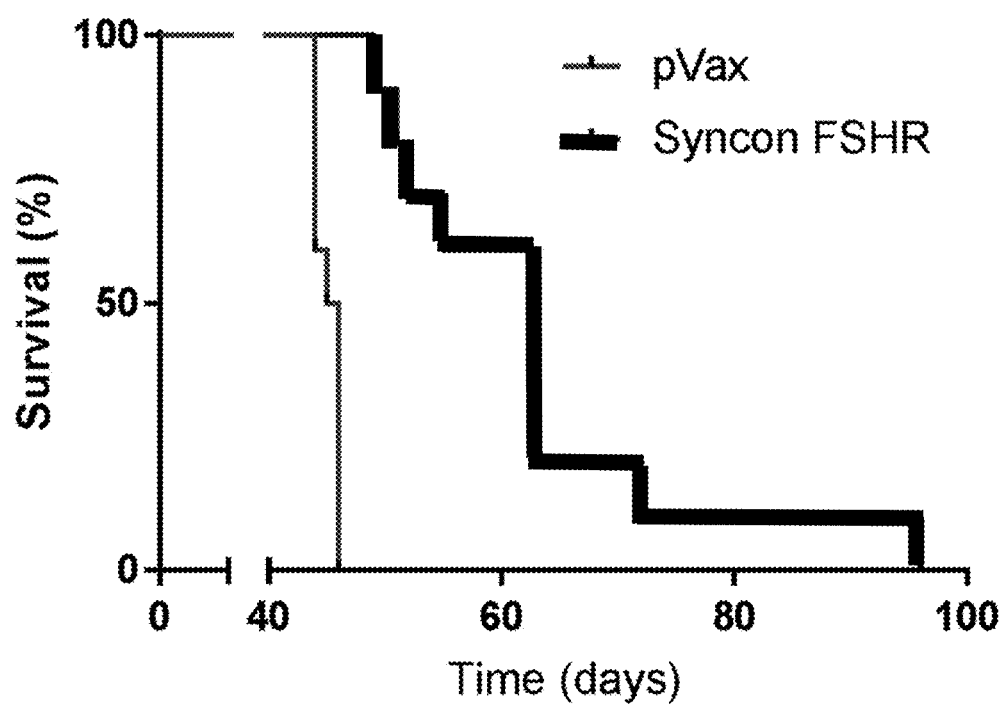
FIG. 13 depicts exemplary experimental results demonstrating that immunization with the consensus FSHR DNA vaccine can increase survival in mice.

Effectiveness of Optimized Consensus FSHR DNA Vaccine Against Ovarian Cancer in Immunocompetent Hosts The anti-tumor activity of optimized consensus FSHR DNA vaccine in ovarian cancer is defined using the ovarian cancer cell line ID8-Defb29/Vegf-a1 (Rutkowski et al., Cancer Cell, 2015:27:27-40; Cubillos-Ruiz et al., Cell, 2015, 161:1527-1538; Stephen et al., Immunity, 2014, 41:427-439). To determine if the optimized consensus FSHR vaccine was able to delay ovarian cancer progression, mice were immunized with consensus FSHR vaccine or pVax empty vector three times in two week intervals. A week after the third immunization the mice were challenged intraperitoneally with 2 million ID8-Defb29/Vegf-a-Fshr ovarian cancer cells. Survival of the mice was followed and a delay of ovarian cancer progression was observed in the mice treated with the consensus FSHR vaccine (FIG. 11 through FIG. 13). Survival, as a readout of effectiveness, is compared to determine the T-cell anti-tumor activity. T-cells are sorted from the lymphatic compartments and co-incubated with dendritic cells pulsed with the same FSHR$^+$ ovarian tumor cell line for IFN-gamma ELISpot assays. Optimized consensus FSHR affects the polyclonal immune response ongoing anti-tumor immune responses through antigen spreading. This may be of critical importance to prevent tumor recurrences even if tumor cells lose the FSHR. Tumor-bearing mice are treated with optimized consensus FSHR vs. mock and FACS-sort T cells from tumor and lymphatic locations, at day 14 after treatment and ELISpots are performed with FSHR-tumor pulsed dendritic cells (Perales-Puchalt et al., Clin Cancer Res. 2016).

Immune checkpoint inhibitors pembrolizumab (αPD-1), nivolumab (αPD-1) and ipilimumab (αCTLA-4) have been tested in ovarian cancer with promising results (Hamanishi et al., J Clin Oncol. 2015, 33:4015-4022; Brahmer et al., N Engl J Med. 2012, 366:2455-2465). Ipilimumab has been tested in combination with irradiated ovarian cancer pulsed dendritic cell vaccines, showing a synergistic effect (Hodi et al., Proc Natl Acad Sci U.S.A. 2003, 100:4712-4717). The optimized consensus FSHR DNA vaccine in combination with αCTLA-4 (clone 9D9) or αPD-1 (clone RMP1-14) shows a synergistic effect on tumor growth in mice.

The Effect of FSHR Vaccine in the Tumor Microenvironment

The composition of the tumor microenvironment of mice with established FSHR$^+$ is evaluated in ovarian tumors at days 20 and 34 after tumor challenge to determine the percentage and numbers of CD4+, CD8+ T cells, and Tregs (Perales-Puchalt et al., Clin Cancer Res. 2016). Samples from spleen, draining (mediastinal) lymph nodes, bone marrow and tumor beds (peritoneal wash) are included. An exhaustive analysis of activation (e.g., CD44, CD69, CD27, CD25) vs. exhaustion (e.g., PD-1, Lag3) shows tumor-specific activation patterns. In addition, central memory differentiation of T cells in BM and lymph nodes is analyzed. The numbers and activation status of dendritic cells (e.g., CD80, CD86, CD40, CD70) myeloid compartment is also analyzed including infiltration by macrophages and myeloid derived suppressor cells.

Determine the Relative Contribution of the Different Immune Compartments to the Optimized Consensus FHSR DNA Anti-Tumor Response The relative contribution of the cellular immune compartment to the optimized consensus FSHR anti-tumor response is tested through treating FSHR$^+$ tumor bearing mice with anti-CD8 or anti-CD4 depleting antibodies. The contribution of antibody responses is tested by adding anti-CD20 depleting antibody after tumor challenge. Together, this establishes the mechanism by which optimized consensus DNA vaccines can break tolerance against self-antigens and promote future improvements in its therapeutic implementation.

Ovarian cancer-bearing mice treated with optimized consensus FSHR DNA vaccine show significantly increased survival (even tumor rejection in some cases), compared to controls, which are further augmented in the presence of checkpoint inhibitors. Additionally, an increased specific anti-tumor activity measured by tumor lysate ELISpot is identified. There is a measurable increase in the polyclonal immune response due to antigen spreading similarly to what was demonstrated using chimeric antigen receptor redirected T-cells (Perales-Puchalt et al., Clin Cancer Res. 2016). Together, these results provide evidence for the therapeutic potential of optimized consensus DNA vaccines targeting the FSHR, and pave the way for subsequent clinical testing. The construction of the polyclonal response could be particularly important for eliciting long-term cures in patients.

Immunization of mice with an optimized consensus FSHR results in an increase in CD8 and CD4 T-cells infiltrating the tumor microenvironment, an higher CD8$^+$/Treg ratio and an increase in the number of activated dendritic cells (CD11c$^+$ MHCII$^+$) and expression of costimulatory molecules (e.g. CD80, CD86, CD40) in the tumor microenvironment and draining lymph nodes. The anti-tumor response is abrogated in the absence of CD8$^+$ T-cells and reduced in the absence of CD4$^+$ T-cells. Together, these data demonstrate the mechanism for the activity of the optimized consensus FSHR DNA vaccine and characterize the expected effects in the treatment of ovarian cancer patients.

The dismal prognosis of ovarian cancer is largely due to the advanced stage at which it is diagnosed. Multiple attempts for developing a screening for ovarian cancer (using CA125 and/or ultrasound) have shown very poor positive predictive values and a high cost per year of life saved, making it not applicable for the early detection of ovarian cancer. Similarly, patients with an increased risk of ovarian cancer (those with BRCA mutations, Lynch syndrome) do not benefit from a tight follow up to achieve an early detection, leaving these patients relying only on oophorectomy to prevent ovarian cancer.

Median age of diagnosis is at 63 years of age, with most of the cancers diagnosed after menopause. Due to the lack of an effective screening, the prophylactic vaccination against FSHR would be a viable approach to prevent the 50-70% of ovarian cancers that express FSHR. At this age, the reproductive activity of FSHR is no longer functional so we would not expect potential adverse effects from this application. As shown in FIG. 13, mice vaccinated prophylactically showing a very important increase in survival when later challenged with FSHR ovarian tumors. Of note, no adverse effects were seen in these experiments. Therefore, the synthetic consensus FSHR vaccines has multiple advantages over standard treatments for ovarian cancer. In addition, the prophylactic administration of the FSHR vaccine therefore has a potential application for protecting women who are at risk for developing ovarian cancer, including post-menopausal women and women who have high risk syndromes.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An immunogenic composition comprising an isolated nucleic acid molecule encoding a peptide comprising the amino acid sequence of SEQ ID NO: 2, 4, 6, 8, 10, or 12.

2. The immunogenic composition of claim 1, wherein the nucleic acid molecule is selected from the group consisting of a DNA molecule and an RNA molecule.

3. The immunogenic composition of claim 1, wherein the nucleic acid molecule comprises a nucleic acid sequence having at least about 99% identity to the nucleic acid sequence of SEQ ID NO: 1, SEQ ID NO: 3, SEQ ID NO: 5, SEQ ID NO: 7, SEQ ID NO: 9, or SEQ ID NO: 11.

4. The immunogenic composition of claim 1, wherein the nucleotide sequence is operably linked to at least one regulatory sequence selected from the group consisting of a start codon, an IgE leader sequence and a stop codon.

5. The immunogenic composition of claim 1, wherein the nucleic acid molecule comprises an expression vector.

6. The immunogenic composition of claim 1, wherein the nucleic acid molecule is incorporated into a viral particle.

7. The immunogenic composition of claim 1, further comprising a pharmaceutically acceptable excipient.

8. The immunogenic composition of claim 1, further comprising an adjuvant.

9. An isolated nucleic acid molecule encoding a peptide comprising the amino acid sequence of SEQ ID NO: 2, 4, 6, 8, 10, or 12.

10. The nucleic acid molecule of claim 9, wherein the nucleic acid molecule is selected from the group consisting of a DNA molecule and an RNA molecule.

11. The nucleic acid molecule of claim 9, wherein the nucleic acid molecule comprises a nucleic acid sequence having at least about 99% identity to the nucleic acid sequence of SEQ ID NO: 1, SEQ ID NO: 3, SEQ ID NO: 5, SEQ ID NO: 7, SEQ ID NO: 9, or SEQ ID NO: 11.

12. The nucleic acid molecule of claim 9, wherein the nucleotide sequence is operably linked to at least one regulatory sequence selected from the group consisting of a start codon, an IgE leader sequence and a stop codon.

* * * * *

SEQUENCE LISTING

```
<160> NUMBER OF SEQ ID NOS: 12

<210> SEQ ID NO 1
<211> LENGTH: 2034
<212> TYPE: DNA
<213> ORGANISM: Artificial Sequence
<220> FEATURE:
<223> OTHER INFORMATION: Optimized consensus human FSHR antigen

<400> SEQUENCE: 1
tgtcatcata ggatttgtca ttgctctaat agggtgttcc tgtgccagga gtccaaggtc      60
actgaaatcc catctgacct gccccggaat gctgtggagc tgagatttgt cctgaccaag     120
ctgagagtga tccctaaagg cgcattcagt ggctttgggg acctggagaa aatcgaaatt     180
tcacagaacg atgtgctgga ggtcatcgaa gctaacgtgt tcagcaacct gccaaagctg     240
cacgagatcc gcattgaaaa agctaacaat ctgctgtaca ttgatcccga agcatttcag     300
aatctgccta acctgcgata tctgctgatc agcaataccg gcattaagca cctgcccgcc     360
gtgcataaga ttcagtccct gcagaaagtc ctgctggaca tccaggataa tatcaacatt     420
cacacagtgg agagaaacag cttcatgggg ctgtcctttg aatctgtcat cctgtggctg     480
aataagaacg gcatccagga gattcataat tgcgcattca acgggacaca gctggacgaa     540
ctgaatctgt ccgataacaa taacctggag gaactgccta acgacgtgtt tcaggggggcc     600 agcggaccag tcatcctgga tatttcccga acaagaatcc acagtctgcc ttcatacggc     660
ctggagaatc tgaagaaact gagagccagg tcaacttata acctgaagaa actgccaagc     720
ctggagaagt tcgtggccct gatggaagct tcactgacct accccagcca ctgctgtgct     780
tttgcaaatt ggcggagaca gatctccgag ctgcatccaa tctgtaacaa atctattctg     840
cggcaggaag tggacgatat gacccaggca cgcgggcagc gagtctccct ggccgaggac     900
gatgaaagct cctactctag aggattcgac atgatgtata gtgagttcga ctttgatctg     960
tgcaatgaag tggtcgatgt gacttgttct cccaagcctg acgccttcaa tccctgcgag    1020
gatatcatgg gctataacat tctgagggtg ctgatctggt ttatctctat tctggctatc    1080
accgggaata tcattgtgct ggtcatcctg attactagtc agtacaagct gaccgtgcct    1140
cgcttcctga tgtgcaacct ggcctttgct gacctgtgca tcgggatcta cctgctgctg    1200
attgccagtg tggatatcca cacaaaatca cagtaccata actatgccat cgactggcag    1260
acaggagctg gctgtgatgc cgctggattc tttaccgtgt tcgccagcga gctgtccgtc    1320
tacaccctga cagctattac tctggcaaga gcccacacta tcacccatgc catgcagctg    1380
gactgcaagg tgcagctgag gcacgcagcc agcgtgatgc tggtcggatg gatcttcgct    1440
tttgcagtgg ccctgttccc aatctttggc atttctagtt acatgaaagt gagcatttgt    1500
ctgcctatgg acatcgattc tccactgagt cagctgtatg tgatgtccct gctggtgctg    1560
aacgtcctgg cttttgtggt catttgcggc tgttacacce atatctatct gacagtgcga    1620
aatcccaaca tcgtctcaag ctcctctgac accaagattg caaaacggat ggccatgctg    1680
```

-continued atcttcacag attttctgtg catggccccc attagcttct ttgctatctc tgcaagtctg 1740
aaggtgcctc tgattacagt ctcaaagagc aaaatcctgc tggtgctgtt ctacccaatt 1800
aattcttgcg ctaacccctt tctgtatgca atcttcacta agaactttag gcgcgacttc 1860
tttattctgc tgagcaaatt cggatgttac gagatgcagg cacagatcta taggacagaa 1920
actagttcaa ccgcccacaa tagccatcct cgcaacggcc actgcagctc cgccccaaga 1980
gtcactaatg gaagcaacta caccctggtc ccactgtctc acctggctca gaac 2034

<210> SEQ ID NO 2
<211> LENGTH: 678
<212> TYPE: PRT
<213> ORGANISM: Artificial Sequence
<220> FEATURE:
<223> OTHER INFORMATION: Consensus human FSHR antigen

<400> SEQUENCE: 2

Cys His His Arg Ile Cys His Cys Ser Asn Arg Val Phe Leu Cys Gln
1 5 10 15

Glu Ser Lys Val Thr Glu Ile Pro Ser Asp Leu Pro Arg Asn Ala Val
20 25 30

Glu Leu Arg Phe Val Leu Thr Lys Leu Arg Val Ile Pro Lys Gly Ala
35 40 45

Phe Ser Gly Phe Gly Asp Leu Glu Lys Ile Glu Ile Ser Gln Asn Asp
50 55 60

Val Leu Glu Val Ile Glu Ala Asn Val Phe Ser Asn Leu Pro Lys Leu
65 70 75 80

His Glu Ile Arg Ile Glu Lys Ala Asn Asn Leu Leu Tyr Ile Asp Pro
85 90 95

Glu Ala Phe Gln Asn Leu Pro Asn Leu Arg Tyr Leu Leu Ile Ser Asn
100 105 110

Thr Gly Ile Lys His Leu Pro Ala Val His Lys Ile Gln Ser Leu Gln
115 120 125

Lys Val Leu Leu Asp Ile Gln Asp Asn Ile Asn Ile His Thr Val Glu
130 135 140

Arg Asn Ser Phe Met Gly Leu Ser Phe Glu Ser Val Ile Leu Trp Leu
145 150 155 160

Asn Lys Asn Gly Ile Gln Glu Ile His Asn Cys Ala Phe Asn Gly Thr
165 170 175

Gln Leu Asp Glu Leu Asn Leu Ser Asp Asn Asn Asn Leu Glu Glu Leu
180 185 190

Pro Asn Asp Val Phe Gln Gly Ala Ser Gly Pro Val Ile Leu Asp Ile
195 200 205

Ser Arg Thr Arg Ile His Ser Leu Pro Ser Tyr Gly Leu Glu Asn Leu
210 215 220

Lys Lys Leu Arg Ala Arg Ser Thr Tyr Asn Leu Lys Lys Leu Pro Ser
225 230 235 240

Leu Glu Lys Phe Val Ala Leu Met Glu Ala Ser Leu Thr Tyr Pro Ser
245 250 255

His Cys Cys Ala Phe Ala Asn Trp Arg Arg Gln Ile Ser Glu Leu His
260 265 270

Pro Ile Cys Asn Lys Ser Ile Leu Arg Gln Glu Val Asp Asp Met Thr
275 280 285

Gln Ala Arg Gly Gln Arg Val Ser Leu Ala Glu Asp Asp Glu Ser Ser
290 295 300

```
Tyr Ser Arg Gly Phe Asp Met Met Tyr Ser Glu Phe Asp Phe Asp Leu
305                 310                 315                 320

Cys Asn Glu Val Val Asp Val Thr Cys Ser Pro Lys Pro Asp Ala Phe
            325                 330                 335

Asn Pro Cys Glu Asp Ile Met Gly Tyr Asn Ile Leu Arg Val Leu Ile
            340                 345                 350

Trp Phe Ile Ser Ile Leu Ala Ile Thr Gly Asn Ile Ile Val Leu Val
            355                 360                 365

Ile Leu Ile Thr Ser Gln Tyr Lys Leu Thr Val Pro Arg Phe Leu Met
370                 375                 380

Cys Asn Leu Ala Phe Ala Asp Leu Cys Ile Gly Ile Tyr Leu Leu Leu
385                 390                 395                 400

Ile Ala Ser Val Asp Ile His Thr Lys Ser Gln Tyr His Asn Tyr Ala
            405                 410                 415

Ile Asp Trp Gln Thr Gly Ala Gly Cys Asp Ala Ala Gly Phe Phe Thr
            420                 425                 430

Val Phe Ala Ser Glu Leu Ser Val Tyr Thr Leu Thr Ala Ile Thr Leu
            435                 440                 445

Ala Arg Ala His Thr Ile Thr His Ala Met Gln Leu Asp Cys Lys Val
450                 455                 460

Gln Leu Arg His Ala Ala Ser Val Met Leu Val Gly Trp Ile Phe Ala
465                 470                 475                 480

Phe Ala Val Ala Leu Phe Pro Ile Phe Gly Ile Ser Ser Tyr Met Lys
            485                 490                 495

Val Ser Ile Cys Leu Pro Met Asp Ile Asp Ser Pro Leu Ser Gln Leu
            500                 505                 510

Tyr Val Met Ser Leu Leu Val Leu Asn Val Leu Ala Phe Val Val Ile
            515                 520                 525

Cys Gly Cys Tyr Thr His Ile Tyr Leu Thr Val Arg Asn Pro Asn Ile
530                 535                 540

Val Ser Ser Ser Ser Asp Thr Lys Ile Ala Lys Arg Met Ala Met Leu
545                 550                 555                 560

Ile Phe Thr Asp Phe Leu Cys Met Ala Pro Ile Ser Phe Phe Ala Ile
            565                 570                 575

Ser Ala Ser Leu Lys Val Pro Leu Ile Thr Val Ser Lys Ser Lys Ile
            580                 585                 590

Leu Leu Val Leu Phe Tyr Pro Ile Asn Ser Cys Ala Asn Pro Phe Leu
            595                 600                 605

Tyr Ala Ile Phe Thr Lys Asn Phe Arg Arg Asp Phe Phe Ile Leu Leu
610                 615                 620

Ser Lys Phe Gly Cys Tyr Glu Met Gln Ala Gln Ile Tyr Arg Thr Glu
625                 630                 635                 640

Thr Ser Ser Thr Ala His Asn Ser His Pro Arg Asn Gly His Cys Ser
            645                 650                 655

Ser Ala Pro Arg Val Thr Asn Gly Ser Asn Tyr Thr Leu Val Pro Leu
            660                 665                 670

Ser His Leu Ala Gln Asn
        675

<210> SEQ ID NO 3
<211> LENGTH: 2088
<212> TYPE: DNA
<213> ORGANISM: Artificial Sequence
<220> FEATURE:
<223> OTHER INFORMATION: Optimized consensus human FSHR antigen operably
``` linked to IgE leader (pGX1424)

<400> SEQUENCE: 3

```
atggactgga cttggattct gtttctggtc gccgccgcta cacgagtgca tagttgtcat      60
cataggattt gtcattgctc taatagggtg ttcctgtgcc aggagtccaa ggtcactgaa     120
atcccatctg acctgccccg gaatgctgtg gagctgagat ttgtcctgac caagctgaga     180
gtgatcccta aggcgcatt cagtggcttt ggggacctgg agaaaatcga atttcacag       240
aacgatgtgc tggaggtcat cgaagctaac gtgttcagca acctgccaaa gctgcacgag     300
atccgcattg aaaaagctaa caatctgctg tacattgatc ccgaagcatt tcagaatctg     360
cctaacctgc gatatctgct gatcagcaat accggcatta agcacctgcc cgccgtgcat     420
aagattcagt ccctgcagaa agtcctgctg gacatccagg ataatatcaa cattcacaca     480
gtggagagaa acagcttcat ggggctgtcc tttgaatctg tcatcctgtg gctgaataag     540
aacggcatcc aggagattca taattgcgca ttcaacggga cacagctgga cgaactgaat     600
ctgtccgata caataaccct ggaggaactg cctaacgacg tgtttcaggg ggccagcgga     660
ccagtcatcc tggatatttc ccgaacaaga atccacagtc tgccttcata cggcctggag     720
aatctgaaga aactgagagc caggtcaact tataacctga gaaactgcc aagcctggag      780
aagttcgtgg ccctgatgga agcttcactg acctacccca gccactgctg tgcttttgca     840
aattggcgga gacagatctc cgagctgcat ccaatctgta caaatctat tctgcggcag     900
gaagtggacg atatgaccca ggcacgcggg cagcgagtct ccctggccga ggacgatgaa     960
agctcctact ctagaggatt cgacatgatg tatagtgagt cgactttga tctgtgcaat    1020
gaagtggtcg atgtgacttg ttctcccaag cctgacgcct caatccctg cgaggatatc    1080
atgggctata acattctgag ggtgctgatc tggtttatct ctattctggc tatcaccggg    1140
aatatcattg tgctggtcat cctgattact agtcagtaca agctgaccgt gcctcgcttc    1200
ctgatgtgca acctggcctt tgctgacctg tgcatcggga tctacctgct gctgattgcc    1260
agtgtggata tccacacaaa atcacagtac cataactatg ccatcgactg cagacagga    1320
gctggctgtg atgccgctgg attctttacc gtgttcgcca gcgagctgtc cgtctacacc    1380
ctgacagcta ttactctggc aagagcccac actatcaccc atgccatgca gctggactgc    1440
aaggtgcagc tgaggcacgc agccagcgtg atgctggtcg atggatcttc gcttttgca    1500
gtggccctgt cccaatcttt ggcatttct agttacatga aagtgagcat tgtctgcct     1560
atggacatcg attctccact gagtcagctg tatgtgatgt ccctgctggt gctgaacgtc     1620
ctggcttttg tggtcatttg cggctgttac acccatatct atctgacagt gcgaaatccc     1680
aacatcgtct caagctcctc tgacaccaag attgcaaaac ggatggccat gctgatcttc     1740
acagatttc tgtgcatggc ccccattagc ttctttgcta tctctgcaag tctgaaggtg     1800
cctctgatta cagtctcaaa gagcaaaatc ctgctggtgc tgttctaccc aattaattct     1860
tgcgctaacc cctttctgta tgcaatcttc actaagaact ttaggcgcga cttctttatt     1920
ctgctgagca aattcggatg ttacgagatg caggcacaga tctataggac agaaactagt     1980
tcaaccgccc acaatagcca tcctcgcaac ggccactgca gctccgcccc aagagtcact     2040
aatggaagca actacaccct ggtcccactg tctcacctgg ctcagaac               2088
```

<210> SEQ ID NO 4
<211> LENGTH: 696
<212> TYPE: PRT
<213> ORGANISM: Artificial Sequence
<220> FEATURE:
<223> OTHER INFORMATION: Consensus human FSHR antigen operably linked to
      IgE leader (pGX1424)

<400> SEQUENCE: 4

Met Asp Trp Thr Trp Ile Leu Phe Leu Val Ala Ala Thr Arg Val
1               5                   10                  15

His Ser Cys His His Arg Ile Cys His Cys Ser Asn Arg Val Phe Leu
            20                  25                  30

Cys Gln Glu Ser Lys Val Thr Glu Ile Pro Ser Asp Leu Pro Arg Asn
        35                  40                  45

Ala Val Glu Leu Arg Phe Val Leu Thr Lys Leu Arg Val Ile Pro Lys
50                  55                  60

Gly Ala Phe Ser Gly Phe Gly Asp Leu Glu Lys Ile Glu Ile Ser Gln
65                  70                  75                  80

Asn Asp Val Leu Glu Val Ile Glu Ala Asn Val Phe Ser Asn Leu Pro
                85                  90                  95

Lys Leu His Glu Ile Arg Ile Glu Lys Ala Asn Asn Leu Leu Tyr Ile
            100                 105                 110

Asp Pro Glu Ala Phe Gln Asn Leu Pro Asn Leu Arg Tyr Leu Leu Ile
        115                 120                 125

Ser Asn Thr Gly Ile Lys His Leu Pro Ala Val His Lys Ile Gln Ser
130                 135                 140

Leu Gln Lys Val Leu Leu Asp Ile Gln Asp Asn Ile Asn Ile His Thr
145                 150                 155                 160

Val Glu Arg Asn Ser Phe Met Gly Leu Ser Phe Glu Ser Val Ile Leu
                165                 170                 175

Trp Leu Asn Lys Asn Gly Ile Gln Glu Ile His Asn Cys Ala Phe Asn
            180                 185                 190

Gly Thr Gln Leu Asp Glu Leu Asn Leu Ser Asp Asn Asn Asn Leu Glu
        195                 200                 205

Glu Leu Pro Asn Asp Val Phe Gln Gly Ala Ser Gly Pro Val Ile Leu
    210                 215                 220

Asp Ile Ser Arg Thr Arg Ile His Ser Leu Pro Ser Tyr Gly Leu Glu
225                 230                 235                 240

Asn Leu Lys Lys Leu Arg Ala Arg Ser Thr Tyr Asn Leu Lys Lys Leu
                245                 250                 255

Pro Ser Leu Glu Lys Phe Val Ala Leu Met Glu Ala Ser Leu Thr Tyr
            260                 265                 270

Pro Ser His Cys Cys Ala Phe Ala Asn Trp Arg Arg Gln Ile Ser Glu
        275                 280                 285

Leu His Pro Ile Cys Asn Lys Ser Ile Leu Arg Gln Glu Val Asp Asp
    290                 295                 300

Met Thr Gln Ala Arg Gly Gln Arg Val Ser Leu Ala Glu Asp Asp Glu
305                 310                 315                 320

Ser Ser Tyr Ser Arg Gly Phe Asp Met Met Tyr Ser Glu Phe Asp Phe
                325                 330                 335

Asp Leu Cys Asn Glu Val Val Asp Val Thr Cys Ser Pro Lys Pro Asp
            340                 345                 350

Ala Phe Asn Pro Cys Glu Asp Ile Met Gly Tyr Asn Ile Leu Arg Val
        355                 360                 365

Leu Ile Trp Phe Ile Ser Ile Leu Ala Ile Thr Gly Asn Ile Ile Val
    370                 375                 380

Leu Val Ile Leu Ile Thr Ser Gln Tyr Lys Leu Thr Val Pro Arg Phe

```
                385                 390                 395                 400
        Leu Met Cys Asn Leu Ala Phe Ala Asp Leu Cys Ile Gly Ile Tyr Leu
                        405                 410                 415
        Leu Leu Ile Ala Ser Val Asp Ile His Thr Lys Ser Gln Tyr His Asn
                        420                 425                 430
        Tyr Ala Ile Asp Trp Gln Thr Gly Ala Gly Cys Asp Ala Ala Gly Phe
                        435                 440                 445
        Phe Thr Val Phe Ala Ser Glu Leu Ser Val Tyr Thr Leu Thr Ala Ile
                        450                 455                 460
        Thr Leu Ala Arg Ala His Thr Ile Thr His Ala Met Gln Leu Asp Cys
        465                 470                 475                 480
        Lys Val Gln Leu Arg His Ala Ala Ser Val Met Leu Val Gly Trp Ile
                        485                 490                 495
        Phe Ala Phe Ala Val Ala Leu Phe Pro Ile Phe Gly Ile Ser Ser Tyr
                        500                 505                 510
        Met Lys Val Ser Ile Cys Leu Pro Met Asp Ile Asp Ser Pro Leu Ser
                        515                 520                 525
        Gln Leu Tyr Val Met Ser Leu Leu Val Leu Asn Val Leu Ala Phe Val
                        530                 535                 540
        Val Ile Cys Gly Cys Tyr Thr His Ile Tyr Leu Thr Val Arg Asn Pro
        545                 550                 555                 560
        Asn Ile Val Ser Ser Ser Asp Thr Lys Ile Ala Lys Arg Met Ala
                        565                 570                 575
        Met Leu Ile Phe Thr Asp Phe Leu Cys Met Ala Pro Ile Ser Phe Phe
                        580                 585                 590
        Ala Ile Ser Ala Ser Leu Lys Val Pro Leu Ile Thr Val Ser Lys Ser
                        595                 600                 605
        Lys Ile Leu Leu Val Leu Phe Tyr Pro Ile Asn Ser Cys Ala Asn Pro
                        610                 615                 620
        Phe Leu Tyr Ala Ile Phe Thr Lys Asn Phe Arg Arg Asp Phe Phe Ile
        625                 630                 635                 640
        Leu Leu Ser Lys Phe Gly Cys Tyr Glu Met Gln Ala Gln Ile Tyr Arg
                        645                 650                 655
        Thr Glu Thr Ser Ser Thr Ala His Asn Ser His Pro Arg Asn Gly His
                        660                 665                 670
        Cys Ser Ser Ala Pro Arg Val Thr Asn Gly Ser Asn Tyr Thr Leu Val
                        675                 680                 685
        Pro Leu Ser His Leu Ala Gln Asn
        690                 695

<210> SEQ ID NO 5
<211> LENGTH: 2025
<212> TYPE: DNA
<213> ORGANISM: Artificial Sequence
<220> FEATURE:
<223> OTHER INFORMATION: Optimized consensus mouse FSHR antigen

<400> SEQUENCE: 5
tgccaccact ggctgtgcca ctgttctaac agggtgttcc tgtgccagga cagcaaggtg      60
accgagatcc ctcccgatct gccccggaac gccatcgagc tgcgcttcgt gctgacaaag     120
ctgagagtga tccctaaggg ctccttctct ggctttggag atctggagaa gatcgagatc     180
tcccagaacg acgtgctgga agtgatcgag gccgacgtgt tcagcaacct gcctaagctg     240
cacgagatcc ggatcgagaa ggccaacaac ctgctgtaca tcaaccccga ggctttccag     300
```

-continued

```
aacctgccta gcctgcgcta cctgctgatc tccaacaccg gcatcaagca cctgccagcc    360
gtgcacaaga tccagagcct gcagaaggtg ctgctggaca tccaggataa catcaacatc    420
cacatcatcg ctagaaactc cttcatggga ctgtcttttg agagcgtgat cctgtggctg    480
aacaagaacg gcatccagga gatccacaac tgtgccttta acggaacaca gctggacgag    540
ctgaacctgt ctgataacaa caacctggag gagctgccta acgacgtgtt ccagggcgcc    600
agcggaccag tgatcctgga tatctccagg accaaggtgc actctctgcc caaccacggc    660
ctggagaacc tgaagaagct gagggccaga tccacataca gactgaagaa gctgccttct    720
ctggacaagt tcgtgaccct gatggaggct tctctgacat acccaagcca ctgctgtgcc    780
tttgctaact ggaggagaca gatcagcgag ctgcacccaa tctgtaacaa gtccatcctg    840
cggcaggaca tcgacgatat gacccagatc ggagatcagc gcgtgagcct gatcgacgat    900
gagccctcct acggcaaggg atctgacatg atgtacagcg agttcgactt tgatctgtgc    960
aacgaggtgg tggatgtgac atgttcccca aagcccgacg ccttcaaccc ctgcgaggat   1020
atcatgggct acaacatcct gcgggtgctg atctggttta tctccatcct ggctatcacc   1080
ggaaacacca cagtgctggt ggtgctgacc acatctcagt acaagctgac agtgcctcgc   1140
ttcctgatgt gcaacctggc ctttgctgac ctgtgcatcg gcatctacct gctgctgatc   1200
gcctctgtgg atatccacac caagagccag taccacaact acgccatcga ctggcagacc   1260
ggcgctggat gtgatgctgc cggattcttt acagtgttcg cctccgagct gagcgtgtac   1320
accctgacag ctatcaccct ggccagggct cacaccatca cacacgccat gcagctggag   1380
tgcaaggtgc agctgagaca cgctgcctct atcatggtgc tgggctggac attcgctttt   1440
gctgccgctc tgttcccaat ctttggaatc agctcctaca tgaaggtgtc catctgtctg   1500
cctatggaca tcgatagccc actgtcccag ctgtacgtga tggccctgct ggtgctgaac   1560
gtgctggcct tcgtggtcat ctgcggctgt tacacccaca tctacctgac agtgcggaac   1620
cccaacatcg tgtctagctc ctctgacacc aagatcgcca agcgcatggc taccctgatc   1680
ttcacagatt ttctgtgcat ggccccaatc agcttctttg ccatcagcgc ctccctgaag   1740
gtgcccctga tcaccgtgag caaggctaag atcctgctgg tgctgttcta cccaatcaac   1800
tcctgcgcca accccttttct gtacgctatc ttcacaaaga actttcggcg cgacttcttt   1860
atcctgatga gcaagttcgg atgttacgag atgcaggccc agatctaccg gaccgagaca   1920
agctccgcca cccacaactt tcacgctagg aagtcccact gcagcagcgc cccccagggtg   1980 acaaactctt acgtgctggt gcctctgaac cacagcgtgc agaac                  2025
```

<210> SEQ ID NO 6
<211> LENGTH: 675
<212> TYPE: PRT
<213> ORGANISM: Artificial Sequence
<220> FEATURE:
<223> OTHER INFORMATION: Consensus mouse FSHR antigen

<400> SEQUENCE: 6

```
Cys His His Trp Leu Cys His Cys Ser Asn Arg Val Phe Leu Cys Gln
1               5                   10                  15

Asp Ser Lys Val Thr Glu Ile Pro Pro Asp Leu Pro Arg Asn Ala Ile
            20                  25                  30

Glu Leu Arg Phe Val Leu Thr Lys Leu Arg Val Ile Pro Lys Gly Ser
        35                  40                  45

Phe Ser Gly Phe Gly Asp Leu Glu Lys Ile Glu Ile Ser Gln Asn Asp
    50                  55                  60
```

```
Val Leu Glu Val Ile Glu Ala Asp Val Phe Ser Asn Leu Pro Lys Leu
 65                  70                  75                  80

His Glu Ile Arg Ile Glu Lys Ala Asn Asn Leu Leu Tyr Ile Asn Pro
                 85                  90                  95

Glu Ala Phe Gln Asn Leu Pro Ser Leu Arg Tyr Leu Leu Ile Ser Asn
            100                 105                 110

Thr Gly Ile Lys His Leu Pro Ala Val His Lys Ile Gln Ser Leu Gln
        115                 120                 125

Lys Val Leu Leu Asp Ile Gln Asp Asn Ile Asn Ile His Ile Ile Ala
    130                 135                 140

Arg Asn Ser Phe Met Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Asn Leu Glu Glu Leu
            180                 185                 190

Pro Asn Asp Val Phe Gln Gly Ala Ser Gly Pro Val Ile Leu Asp Ile
        195                 200                 205

Ser Arg Thr Lys Val His Ser Leu Pro Asn His Gly Leu Glu Asn Leu
    210                 215                 220

Lys Lys Leu Arg Ala Arg Ser Thr Tyr Arg Leu Lys Lys Leu Pro Ser
225                 230                 235                 240

Leu Asp Lys Phe Val Thr Leu Met Glu Ala Ser Leu Thr Tyr Pro Ser
                245                 250                 255

His Cys Cys Ala Phe Ala Asn Trp Arg Arg Gln Ile Ser Glu Leu His
            260                 265                 270

Pro Ile Cys Asn Lys Ser Ile Leu Arg Gln Asp Ile Asp Asp Met Thr
        275                 280                 285

Gln Ile Gly Asp Gln Arg Val Ser Leu Ile Asp Asp Glu Pro Ser Tyr
    290                 295                 300

Gly Lys Gly Ser Asp Met Met Tyr Ser Glu Phe Asp Phe Asp Leu Cys
305                 310                 315                 320

Asn Glu Val Val Asp Val Thr Cys Ser Pro Lys Pro Asp Ala Phe Asn
                325                 330                 335

Pro Cys Glu Asp Ile Met Gly Tyr Asn Ile Leu Arg Val Leu Ile Trp
            340                 345                 350

Phe Ile Ser Ile Leu Ala Ile Thr Gly Asn Thr Thr Val Leu Val Val
        355                 360                 365

Leu Thr Thr Ser Gln Tyr Lys Leu Thr Val Pro Arg Phe Leu Met Cys
    370                 375                 380

Asn Leu Ala Phe Ala Asp Leu Cys Ile Gly Ile Tyr Leu Leu Leu Ile
385                 390                 395                 400

Ala Ser Val Asp Ile His Thr Lys Ser Gln Tyr His Asn Tyr Ala Ile
                405                 410                 415

Asp Trp Gln Thr Gly Ala Gly Cys Asp Ala Ala Gly Phe Phe Thr Val
            420                 425                 430

Phe Ala Ser Glu Leu Ser Val Tyr Thr Leu Thr Ala Ile Thr Leu Ala
        435                 440                 445

Arg Ala His Thr Ile Thr His Ala Met Gln Leu Glu Cys Lys Val Gln
    450                 455                 460

Leu Arg His Ala Ala Ser Ile Met Val Leu Gly Trp Thr Phe Ala Phe
465                 470                 475                 480
```

Ala Ala Ala Leu Phe Pro Ile Phe Gly Ile Ser Ser Tyr Met Lys Val
            485                 490                 495

Ser Ile Cys Leu Pro Met Asp Ile Asp Ser Pro Leu Ser Gln Leu Tyr
        500                 505                 510

Val Met Ala Leu Leu Val Leu Asn Val Leu Ala Phe Val Val Ile Cys
        515                 520                 525

Gly Cys Tyr Thr His Ile Tyr Leu Thr Val Arg Asn Pro Asn Ile Val
        530                 535                 540

Ser Ser Ser Asp Thr Lys Ile Ala Lys Arg Met Ala Thr Leu Ile
545                 550                 555                 560

Phe Thr Asp Phe Leu Cys Met Ala Pro Ile Ser Phe Phe Ala Ile Ser
                565                 570                 575

Ala Ser Leu Lys Val Pro Leu Ile Thr Val Ser Lys Ala Lys Ile Leu
            580                 585                 590

Leu Val Leu Phe Tyr Pro Ile Asn Ser Cys Ala Asn Pro Phe Leu Tyr
        595                 600                 605

Ala Ile Phe Thr Lys Asn Phe Arg Arg Asp Phe Phe Ile Leu Met Ser
        610                 615                 620

Lys Phe Gly Cys Tyr Glu Met Gln Ala Gln Ile Tyr Arg Thr Glu Thr
625                 630                 635                 640

Ser Ser Ala Thr His Asn Phe His Ala Arg Lys Ser His Cys Ser Ser
                645                 650                 655

Ala Pro Arg Val Thr Asn Ser Tyr Val Leu Val Pro Leu Asn His Ser
            660                 665                 670

Val Gln Asn
        675

<210> SEQ ID NO 7
<211> LENGTH: 2079
<212> TYPE: DNA
<213> ORGANISM: Artificial Sequence
<220> FEATURE:
<223> OTHER INFORMATION: Optimized consensus mouse FSHR antigen operably
      linked to IgE leader

<400> SEQUENCE: 7
atggactgga cctggattct gttcctggtg ccgctgcca caagggtgca ctcctgccac    60
cactggctgt gccactgttc taacagggtg ttcctgtgcc aggacagcaa ggtgaccgag   120
atccctcccg atctgccccg gaacgccatc gagctgcgct tcgtgctgac aaagctgaga   180
gtgatcccta agggctcctt ctctggcttt ggagatctgg agaagatcga gatctcccag   240
aacgacgtgc tggaagtgat cgaggccgac gtgttcagca acctgctaa gctgcacgag   300 atccggatcg agaaggccaa caacctgctg tacatcaacc ccgaggcttt ccagaacctg   360
cctagcctgc gctacctgct gatctccaac accggcatca gcacctgcc agccgtgcac   420 aagatccaga gcctgcagaa ggtgctgctg acatccagg ataacatcaa catccacatc   480
atcgctagaa actccttcat gggactgtct tttgagagcg tgatcctgtg gctgaacaag   540
aacggcatcc aggagatcca aactgtgcc tttaacggaa cacagctgga cgagctgaac   600
ctgtctgata caacaacct ggaggagctg cctaacgacg tgttccaggg cgccagcgga   660
ccagtgatcc tggatatctc caggaccaag gtgcactctc tgcccaacca cggcctggag   720
aacctgaaga gctgagggc cagatccaca tacagactga agaagctgcc ttctctggac   780
aagttcgtga ccctgatgga ggcttctctg acatacccaa gccactgctg tgcctttgct   840
aactggagga gacagatcag cgagctgcac ccaatctgta caagtccat cctgcggcag   900

-continued

```
gacatcgacg atatgaccca gatcggagat cagcgcgtga gcctgatcga cgatgagccc    960
tcctacggca agggatctga catgatgtac agcgagttcg actttgatct gtgcaacgag   1020
gtggtggatg tgacatgttc cccaaagccc gacgccttca accccctgcga ggatatcatg   1080 ggctacaaca tcctgcgggt gctgatctgg tttatctcca tcctggctat caccggaaac   1140
accacagtgc tggtggtgct gaccacatct cagtacaagc tgacagtgcc tcgcttcctg   1200
atgtgcaacc tggcctttgc tgacctgtgc atcggcatct acctgctgct gatcgcctct   1260
gtggatatcc acaccaagag ccagtaccac aactacgcca tcgactggca gaccggcgct   1320
ggatgtgatg ctgccggatt ctttacagtg ttcgcctccg agctgagcgt gtacaccctg   1380
acagctatca ccctggccag ggctcacacc atcacacacg ccatgcagct ggagtgcaag   1440
gtgcagctga gacacgctgc ctctatcatg gtgctgggct ggacattcgc ttttgctgcc   1500
gctctgttcc caatctttgg aatcagctcc tacatgaagg tgtccatctg tctgcctatg   1560
gacatcgata gcccactgtc ccagctgtac gtgatggccc tgctggtgct gaacgtgctg   1620
gccttcgtgg tcatctgcgg ctgttacacc cacatctacc tgacagtgcg gaaccccaac   1680
atcgtgtcta gctcctctga caccaagatc gccaagcgca tggctaccct gatcttcaca   1740
gattttctgt gcatggcccc aatcagcttc tttgccatca gcgcctccct gaaggtgccc   1800
ctgatcaccg tgagcaaggc taagatcctg ctggtgctgt tctacccaat caactcctgc   1860
gccaacccct ttctgtacgc tatcttcaca aagaactttc ggcgcgactt ctttatcctg   1920
atgagcaagt tcggatgtta cgagatgcag gcccagatct accggaccga gacaagctcc   1980
gccacccaca actttcacgc taggaagtcc cactgcagca gcgcccccag ggtgacaaac   2040
tcttacgtgc tggtgcctct gaaccacagc gtgcagaac                          2079
```

<210> SEQ ID NO 8
<211> LENGTH: 693
<212> TYPE: PRT
<213> ORGANISM: Artificial Sequence
<220> FEATURE:
<223> OTHER INFORMATION: Consensus mouse FSHR antigen operably linked to
      IgE leader

<400> SEQUENCE: 8

```
Met Asp Trp Thr Trp Ile Leu Phe Leu Val Ala Ala Thr Arg Val
1               5                   10                  15

His Ser Cys His His Trp Leu Cys His Cys Ser Asn Arg Val Phe Leu
                20                  25                  30

Cys Gln Asp Ser Lys Val Thr Glu Ile Pro Pro Asp Leu Pro Arg Asn
            35                  40                  45

Ala Ile Glu Leu Arg Phe Val Leu Thr Lys Leu Arg Val Ile Pro Lys
        50                  55                  60

Gly Ser Phe Ser Gly Phe Gly Asp Leu Glu Lys Ile Glu Ile Ser Gln
65                  70                  75                  80

Asn Asp Val Leu Glu Val Ile Glu Ala Asp Val Phe Ser Asn Leu Pro
                85                  90                  95

Lys Leu His Glu Ile Arg Ile Glu Lys Ala Asn Asn Leu Leu Tyr Ile
                100                 105                 110

Asn Pro Glu Ala Phe Gln Asn Leu Pro Ser Leu Arg Tyr Leu Leu Ile
            115                 120                 125

Ser Asn Thr Gly Ile Lys His Leu Pro Ala Val His Lys Ile Gln Ser
        130                 135                 140
```

```
Leu Gln Lys Val Leu Leu Asp Ile Gln Asp Asn Ile Asn Ile His Ile
145                 150                 155                 160

Ile Ala Arg Asn Ser Phe Met Gly Leu Ser Phe Glu Ser Val Ile Leu
                165                 170                 175

Trp Leu Asn Lys Asn Gly Ile Gln Glu Ile His Asn Cys Ala Phe Asn
            180                 185                 190

Gly Thr Gln Leu Asp Glu Leu Asn Leu Ser Asp Asn Asn Asn Leu Glu
        195                 200                 205

Glu Leu Pro Asn Asp Val Phe Gln Gly Ala Ser Gly Pro Val Ile Leu
    210                 215                 220

Asp Ile Ser Arg Thr Lys Val His Ser Leu Pro Asn His Gly Leu Glu
225                 230                 235                 240

Asn Leu Lys Lys Leu Arg Ala Arg Ser Thr Tyr Arg Leu Lys Lys Leu
                245                 250                 255

Pro Ser Leu Asp Lys Phe Val Thr Leu Met Glu Ala Ser Leu Thr Tyr
                260                 265                 270

Pro Ser His Cys Cys Ala Phe Ala Asn Trp Arg Arg Gln Ile Ser Glu
            275                 280                 285

Leu His Pro Ile Cys Asn Lys Ser Ile Leu Arg Gln Asp Ile Asp Asp
        290                 295                 300

Met Thr Gln Ile Gly Asp Gln Arg Val Ser Leu Ile Asp Asp Glu Pro
305                 310                 315                 320

Ser Tyr Gly Lys Gly Ser Asp Met Met Tyr Ser Glu Phe Asp Phe Asp
                325                 330                 335

Leu Cys Asn Glu Val Val Asp Val Thr Cys Ser Pro Lys Pro Asp Ala
                340                 345                 350

Phe Asn Pro Cys Glu Asp Ile Met Gly Tyr Asn Ile Leu Arg Val Leu
            355                 360                 365

Ile Trp Phe Ile Ser Ile Leu Ala Ile Thr Gly Asn Thr Thr Val Leu
        370                 375                 380

Val Val Leu Thr Thr Ser Gln Tyr Lys Leu Thr Val Pro Arg Phe Leu
385                 390                 395                 400

Met Cys Asn Leu Ala Phe Ala Asp Leu Cys Ile Gly Ile Tyr Leu Leu
                405                 410                 415

Leu Ile Ala Ser Val Asp Ile His Thr Lys Ser Gln Tyr His Asn Tyr
                420                 425                 430

Ala Ile Asp Trp Gln Thr Gly Ala Gly Cys Asp Ala Ala Gly Phe Phe
            435                 440                 445

Thr Val Phe Ala Ser Glu Leu Ser Val Tyr Thr Leu Thr Ala Ile Thr
        450                 455                 460

Leu Ala Arg Ala His Thr Ile Thr His Ala Met Gln Leu Glu Cys Lys
465                 470                 475                 480

Val Gln Leu Arg His Ala Ala Ser Ile Met Val Leu Gly Trp Thr Phe
                485                 490                 495

Ala Phe Ala Ala Ala Leu Phe Pro Ile Phe Gly Ile Ser Ser Tyr Met
                500                 505                 510

Lys Val Ser Ile Cys Leu Pro Met Asp Ile Asp Ser Pro Leu Ser Gln
            515                 520                 525

Leu Tyr Val Met Ala Leu Leu Val Leu Asn Val Leu Ala Phe Val Val
        530                 535                 540

Ile Cys Gly Cys Tyr Thr His Ile Tyr Leu Thr Val Arg Asn Pro Asn
545                 550                 555                 560

Ile Val Ser Ser Ser Ser Asp Thr Lys Ile Ala Lys Arg Met Ala Thr
```

```
              565                 570                 575
Leu Ile Phe Thr Asp Phe Leu Cys Met Ala Pro Ile Ser Phe Phe Ala
            580                 585                 590

Ile Ser Ala Ser Leu Lys Val Pro Leu Ile Thr Val Ser Lys Ala Lys
            595                 600                 605

Ile Leu Leu Val Leu Phe Tyr Pro Ile Asn Ser Cys Ala Asn Pro Phe
        610                 615                 620

Leu Tyr Ala Ile Phe Thr Lys Asn Phe Arg Arg Asp Phe Phe Ile Leu
625                 630                 635                 640

Met Ser Lys Phe Gly Cys Tyr Glu Met Gln Ala Gln Ile Tyr Arg Thr
                645                 650                 655

Glu Thr Ser Ser Ala Thr His Asn Phe His Ala Arg Lys Ser His Cys
            660                 665                 670

Ser Ser Ala Pro Arg Val Thr Asn Ser Tyr Val Leu Val Pro Leu Asn
            675                 680                 685

His Ser Val Gln Asn
        690
```

<210> SEQ ID NO 9
<211> LENGTH: 2034
<212> TYPE: DNA
<213> ORGANISM: Artificial Sequence
<220> FEATURE:
<223> OTHER INFORMATION: Optimized consensus canine FSHR antigen

<400> SEQUENCE: 9

```
tgtcaccaca gaatctgcca ctgcagcaac cgggtgttcc tgtgccaaga gtccaaagtg      60
acagagatcc ccagcgacct gcctcggaat gccgtggaac tgagattcgt gctgaccaag     120
ctgagagtga tccccaaggg cgcctttagc ggcttcggcg acctggaaaa gatcgagatc     180
agccagaacg acgtgctgga agtgatcgag gccaacgtgt tcagcaacct gcctaagctg     240
cacgagatca gaatcgagaa ggccaacaac ctgctgtaca tcgaccccga cgccttccag     300
aacctgccaa acctgagata cctgctgatc tccaacaccg gcatcaaaca tctgcccgcc     360
gtgcacaaga tccagagcct gcagaaagtg ctgctggaca tccaggacaa catcaacatc     420
cacaccgtgg aacggaacag cttcatgggc ctgagcttcg agagcatgat cctgtggctg     480
aacaagaacg gcatccaaga gatccacaac tgcgccttca cggcacccca gctggacgag     540
ctgaacctga gcgacaacaa caatctggaa gaactgccca cgacgtgtt ccagggcgct     600
tctggaccag tgatcctgga catcagccgg accagaatcc acagcctgcc tagctacggc     660
ctggaaaacc tgaagaagct gcgggccaag agcacctaca atctgaaaaa gctgcctagc     720
ctcgagaagt tcgtggccct gatggaagcc agcctgacat accctagcca ctgctgcgcc     780
tttgccaact ggcggagaca gatctctgag ctgcaccca tctgcaacaa gagcatcctg     840
cggcaagagg tggacgacat gacacaggcc agaggccaga gagtgtctct ggccgaggat     900
gacgagagca gctacgccaa gggcttcgac atgatgtact ccgagttcga cgccgacctg     960
tgcaacgagg tggtggatgt gacatgcagc cccaagcctg acgccttcaa tccctgcgag    1020
gacatcatgg gctacgacat cctgagagtg ctgatctggt tcatcagcat cctggccatt    1080
accggcaaca tcatcgtgct ggtcatcctg atcaccagcc agtacaagct gaccgtgcct    1140
cggttcctga tgtgcaatct ggccttcgcc gatctgtgta tcggcatcta cctgctgctg    1200
atcgccagcg tggacattca caccaagagc cagtaccaca ctacgccat cgactggcag    1260
acaggcgccg gatgtgatgc cgccggattc tttacagtgt tcgccagcga gctgagcgtg    1320
```

```
tacaccctga cagccatcac actggccagg gctcacacaa tcacacacgc catgcagctg   1380
gaatgcaagg tgcagctgag acacgccgcc tctgtgatgc tcgtcggatg gatcttcgcc   1440
ttcgctgtgg ccctgtttcc tatcttcggc atcagcagct acatgaaggt gtccatctgc   1500
ctgcctatgg acatcgacag ccctctgagc cagctgtacg tgatgtctct gctggtgctg   1560
aacgtgctgg cctttgtggt catctgcggc tgctacgccc acatctatct gacagtgcgg   1620
aaccccaaca tcgtgtccag ctccagcgat accaagatcg ccaagcggat ggccatgctg   1680
atcttcaccg actttctgtg tatggccccg atcagcttct ttgccatcag cgcttccctg   1740
aaggtgccac tgatcaccgt gtccaagtcc aagatcctgc tggtcctgtt ctaccccatc   1800
aacagctgcg ccaatccttt cctgtacgcc atcttcacca agaacttccg gcgggacttc   1860
ttcatcctgc tgagcaagtt cggctgttac gagattcagg cccagaccta ccggaccgag   1920
acaagctcta cagcccacaa ctctcacccc agaaacggcc actgtcctcc agctcctaga   1980
gtgaccaacg gcagcaacta caccctggtg cctctgtctc atctggccca gaac         2034

<210> SEQ ID NO 10
<211> LENGTH: 678
<212> TYPE: PRT
<213> ORGANISM: Artificial Sequence
<220> FEATURE:
<223> OTHER INFORMATION: Consensus canine FSHR antigen

<400> SEQUENCE: 10

Cys His His Arg Ile Cys His Cys Ser Asn Arg Val Phe Leu Cys Gln
1               5                   10                  15

Glu Ser Lys Val Thr Glu Ile Pro Ser Asp Leu Pro Arg Asn Ala Val
            20                  25                  30

Glu Leu Arg Phe Val Leu Thr Lys Leu Arg Val Ile Pro Lys Gly Ala
        35                  40                  45

Phe Ser Gly Phe Gly Asp Leu Glu Lys Ile Glu Ile Ser Gln Asn Asp
    50                  55                  60

Val Leu Glu Val Ile Glu Ala Asn Val Phe Ser Asn Leu Pro Lys Leu
65                  70                  75                  80

His Glu Ile Arg Ile Glu Lys Ala Asn Asn Leu Leu Tyr Ile Asp Pro
                85                  90                  95

Asp Ala Phe Gln Asn Leu Pro Asn Leu Arg Tyr Leu Leu Ile Ser Asn
            100                 105                 110

Thr Gly Ile Lys His Leu Pro Ala Val His Lys Ile Gln Ser Leu Gln
        115                 120                 125

Lys Val Leu Leu Asp Ile Gln Asp Asn Ile Asn Ile His Thr Val Glu
    130                 135                 140

Arg Asn Ser Phe Met Gly Leu Ser Phe Glu Ser Met Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Asn Leu Glu Glu Leu
            180                 185                 190

Pro Asn Asp Val Phe Gln Gly Ala Ser Gly Pro Val Ile Leu Asp Ile
        195                 200                 205

Ser Arg Thr Arg Ile His Ser Leu Pro Ser Tyr Gly Leu Glu Asn Leu
    210                 215                 220

Lys Lys Leu Arg Ala Lys Ser Thr Tyr Asn Leu Lys Lys Leu Pro Ser
225                 230                 235                 240
```

```
Leu Glu Lys Phe Val Ala Leu Met Glu Ala Ser Leu Thr Tyr Pro Ser
                245                 250                 255

His Cys Cys Ala Phe Ala Asn Trp Arg Arg Gln Ile Ser Glu Leu His
            260                 265                 270

Pro Ile Cys Asn Lys Ser Ile Leu Arg Gln Val Asp Asp Met Thr
        275                 280                 285

Gln Ala Arg Gly Gln Arg Val Ser Leu Ala Glu Asp Asp Glu Ser Ser
    290                 295                 300

Tyr Ala Lys Gly Phe Asp Met Met Tyr Ser Glu Phe Asp Ala Asp Leu
305                 310                 315                 320

Cys Asn Glu Val Val Asp Val Thr Cys Ser Pro Lys Pro Asp Ala Phe
                325                 330                 335

Asn Pro Cys Glu Asp Ile Met Gly Tyr Asp Ile Leu Arg Val Leu Ile
            340                 345                 350

Trp Phe Ile Ser Ile Leu Ala Ile Thr Gly Asn Ile Ile Val Leu Val
        355                 360                 365

Ile Leu Ile Thr Ser Gln Tyr Lys Leu Thr Val Pro Arg Phe Leu Met
    370                 375                 380

Cys Asn Leu Ala Phe Ala Asp Leu Cys Ile Gly Ile Tyr Leu Leu Leu
385                 390                 395                 400

Ile Ala Ser Val Asp Ile His Thr Lys Ser Gln Tyr His Asn Tyr Ala
                405                 410                 415

Ile Asp Trp Gln Thr Gly Ala Gly Cys Asp Ala Ala Gly Phe Phe Thr
            420                 425                 430

Val Phe Ala Ser Glu Leu Ser Val Tyr Thr Leu Thr Ala Ile Thr Leu
        435                 440                 445

Ala Arg Ala His Thr Ile Thr His Ala Met Gln Leu Glu Cys Lys Val
    450                 455                 460

Gln Leu Arg His Ala Ala Ser Val Met Leu Val Gly Trp Ile Phe Ala
465                 470                 475                 480

Phe Ala Val Ala Leu Phe Pro Ile Phe Gly Ile Ser Ser Tyr Met Lys
                485                 490                 495

Val Ser Ile Cys Leu Pro Met Asp Ile Asp Ser Pro Leu Ser Gln Leu
            500                 505                 510

Tyr Val Met Ser Leu Leu Val Leu Asn Val Leu Ala Phe Val Val Ile
        515                 520                 525

Cys Gly Cys Tyr Ala His Ile Tyr Leu Thr Val Arg Asn Pro Asn Ile
    530                 535                 540

Val Ser Ser Ser Ser Asp Thr Lys Ile Ala Lys Arg Met Ala Met Leu
545                 550                 555                 560

Ile Phe Thr Asp Phe Leu Cys Met Ala Pro Ile Ser Phe Phe Ala Ile
                565                 570                 575

Ser Ala Ser Leu Lys Val Pro Leu Ile Thr Val Ser Lys Ser Lys Ile
            580                 585                 590

Leu Leu Val Leu Phe Tyr Pro Ile Asn Ser Cys Ala Asn Pro Phe Leu
        595                 600                 605

Tyr Ala Ile Phe Thr Lys Asn Phe Arg Arg Asp Phe Phe Ile Leu Leu
    610                 615                 620

Ser Lys Phe Gly Cys Tyr Glu Ile Gln Ala Gln Thr Tyr Arg Thr Glu
625                 630                 635                 640

Thr Ser Ser Thr Ala His Asn Ser His Pro Arg Asn Gly His Cys Pro
                645                 650                 655
```

```
Pro Ala Pro Arg Val Thr Asn Gly Ser Asn Tyr Thr Leu Val Pro Leu
            660                 665                 670

Ser His Leu Ala Gln Asn
        675

<210> SEQ ID NO 11
<211> LENGTH: 2088
<212> TYPE: DNA
<213> ORGANISM: Artificial Sequence
<220> FEATURE:
<223> OTHER INFORMATION: Optimized consensus canine FSHR antigen
      operably linked to IgE leader

<400> SEQUENCE: 11
atggattgga cctggatcct gtttctggtg ccgctgcca caagagtgca cagctgtcac        60
cacagaatct gccactgcag caaccgggtg ttcctgtgcc aagagtccaa agtgacagag      120
atccccagcg acctgcctcg aatgccgtg gaactgagat cgtgctgac aagctgaga        180 gtgatcccca agggcgcctt tagcggcttc ggcgacctgg aaaagatcga gatcagccag      240
aacgacgtgc tggaagtgat cgaggccaac gtgttcagca acctgcctaa gctgcacgag      300
atcagaatcg agaaggccaa caacctgctg tacatcgacc ccgacgcctt ccagaacctg      360
ccaaacctga gatacctgct gatctccaac accggcatca acatctgcc cgccgtgcac      420 aagatccaga gcctgcagaa gtgctgctg gacatccagg acaacatcaa catccacacc      480
gtggaacgga cagcttcat gggcctgagc ttcgagagca tgatcctgtg gctgaacaag      540
aacggcatcc aagagatcca aactgcgcc ttcaacggca cccagctgga cgagctgaac      600
ctgagcgaca caacaatct ggaagaactg cccaacgacg tgttccaggg cgcttctgga      660
ccagtgatcc tggacatcag ccggaccaga atccacagcc tgcctagcta cggcctggaa      720
aacctgaaga agctgcgggc caagagcacc tacaatctga aaagctgcc tagcctcgag      780 aagttcgtgg ccctgatgga agccagcctg acatacccta gccactgctg cgcctttgcc      840
aactggcgga gacagatctc tgagctgcac cccatctgca caagagcat cctgcggcaa      900 gaggtggacg acatgacaca ggccagaggc cagagagtgt ctctggccga ggatgacgag      960
agcagctacg ccaagggctt cgacatgatg tactccgagt cgacgccga cctgtgcaac     1020 gaggtggtgg atgtgacatg cagccccaag cctgacgcct tcaatccctg cgaggacatc     1080
atgggctacg acatcctgag agtgctgatc tggttcatca gcatcctggc cattaccggc     1140
aacatcatcg tgctggtcat cctgatcacc agccagtaca gctgaccgt gcctcggttc     1200 ctgatgtgca atctggcctt cgccgatctg tgtatcggc tctacctgct gctgatcgcc     1260
agcgtggaca ttcacaccaa gagccagtac cacaactacg ccatcgactg gcagacaggc     1320
gccggatgtg atgccgccgg attctttaca gtgttcgcca gcgagctgag cgtgtacacc     1380
ctgacagcca tcacactggc cagggctcac acaatcacac acgccatgca gctggaatgc     1440
aaggtgcagc tgagacacgc cgcctctgtg atgctcgtcg atggatcttc gccttcgct     1500 gtggccctgt tcctatctt cggcatcagc agctacatga aggtgtccat ctgcctgcct     1560
atggacatcg acagccctct gagccagctg tacgtgatgt ctctgctggt gctgaacgtg     1620
ctggcctttg tggtcatctg cggctgctac gcccacatct atctgacagt gcggaacccc     1680
aacatcgtgt ccagctccag cgataccaag atcgccaagc ggatggccat gctgatcttc     1740
accgactttc tgtgtatggc cccgatcagc ttctttgcca tcagcgcttc cctgaaggtg     1800
ccactgatca ccgtgtccaa gtccaagatc ctgctggtcc tgttctaccc catcaacagc     1860
```

-continued

```
tgcgccaatc ctttcctgta cgccatcttc accaagaact tccggcggga cttcttcatc   1920
ctgctgagca agttcggctg ttacgagatt caggcccaga cctaccggac cgagacaagc   1980
tctacagccc acaactctca ccccagaaac ggccactgtc ctccagctcc tagagtgacc   2040
aacggcagca actacaccct ggtgcctctg tctcatctgg cccagaac                2088
```

```

<210> SEQ ID NO 12
<211> LENGTH: 696
<212> TYPE: PRT
<213> ORGANISM: Artificial Sequence
<220> FEATURE:
<223> OTHER INFORMATION: Consensus canine FSHR antigen operably linked
      to IgE leader

<400> SEQUENCE: 12

Met Asp Trp Thr Trp Ile Leu Phe Leu Val Ala Ala Ala Thr Arg Val
1               5                   10                  15

His Ser Cys His His Arg Ile Cys His Cys Ser Asn Arg Val Phe Leu
            20                  25                  30

Cys Gln Glu Ser Lys Val Thr Glu Ile Pro Ser Asp Leu Pro Arg Asn
        35                  40                  45

Ala Val Glu Leu Arg Phe Val Leu Thr Lys Leu Arg Val Ile Pro Lys
    50                  55                  60

Gly Ala Phe Ser Gly Phe Gly Asp Leu Glu Lys Ile Glu Ile Ser Gln
65                  70                  75                  80

Asn Asp Val Leu Glu Val Ile Glu Ala Asn Val Phe Ser Asn Leu Pro
                85                  90                  95

Lys Leu His Glu Ile Arg Ile Glu Lys Ala Asn Asn Leu Leu Tyr Ile
            100                 105                 110

Asp Pro Asp Ala Phe Gln Asn Leu Pro Asn Leu Arg Tyr Leu Leu Ile
        115                 120                 125

Ser Asn Thr Gly Ile Lys His Leu Pro Ala Val His Lys Ile Gln Ser
    130                 135                 140

Leu Gln Lys Val Leu Leu Asp Ile Gln Asp Asn Ile Asn Ile His Thr
145                 150                 155                 160

Val Glu Arg Asn Ser Phe Met Gly Leu Ser Phe Glu Ser Met Ile Leu
                165                 170                 175

Trp Leu Asn Lys Asn Gly Ile Gln Glu Ile His Asn Cys Ala Phe Asn
            180                 185                 190

Gly Thr Gln Leu Asp Glu Leu Asn Leu Ser Asp Asn Asn Asn Leu Glu
        195                 200                 205

Glu Leu Pro Asn Asp Val Phe Gln Gly Ala Ser Gly Pro Val Ile Leu
    210                 215                 220

Asp Ile Ser Arg Thr Arg Ile His Ser Leu Pro Ser Tyr Gly Leu Glu
225                 230                 235                 240

Asn Leu Lys Lys Leu Arg Ala Lys Ser Thr Tyr Asn Leu Lys Lys Leu
                245                 250                 255

Pro Ser Leu Glu Lys Phe Val Ala Leu Met Glu Ala Ser Leu Thr Tyr
            260                 265                 270

Pro Ser His Cys Cys Ala Phe Ala Asn Trp Arg Arg Gln Ile Ser Glu
        275                 280                 285

Leu His Pro Ile Cys Asn Lys Ser Ile Leu Arg Gln Glu Val Asp Asp
    290                 295                 300

Met Thr Gln Ala Arg Gly Gln Arg Val Ser Leu Ala Glu Asp Asp Glu
305                 310                 315                 320
```

-continued

```
Ser Ser Tyr Ala Lys Gly Phe Asp Met Met Tyr Ser Glu Phe Asp Ala
                325                 330                 335

Asp Leu Cys Asn Glu Val Val Asp Val Thr Cys Ser Pro Lys Pro Asp
                340                 345                 350

Ala Phe Asn Pro Cys Glu Asp Ile Met Gly Tyr Asp Ile Leu Arg Val
                355                 360                 365

Leu Ile Trp Phe Ile Ser Ile Leu Ala Ile Thr Gly Asn Ile Ile Val
                370                 375             380

Leu Val Ile Leu Ile Thr Ser Gln Tyr Lys Leu Thr Val Pro Arg Phe
385                 390                 395                 400

Leu Met Cys Asn Leu Ala Phe Ala Asp Leu Cys Ile Gly Ile Tyr Leu
                405                 410                 415

Leu Leu Ile Ala Ser Val Asp Ile His Thr Lys Ser Gln Tyr His Asn
                420                 425                 430

Tyr Ala Ile Asp Trp Gln Thr Gly Ala Gly Cys Asp Ala Ala Gly Phe
                435                 440                 445

Phe Thr Val Phe Ala Ser Glu Leu Ser Val Tyr Thr Leu Thr Ala Ile
                450                 455                 460

Thr Leu Ala Arg Ala His Thr Ile Thr His Ala Met Gln Leu Glu Cys
465                 470                 475                 480

Lys Val Gln Leu Arg His Ala Ala Ser Val Met Leu Val Gly Trp Ile
                485                 490                 495

Phe Ala Phe Ala Val Ala Leu Phe Pro Ile Phe Gly Ile Ser Ser Tyr
                500                 505                 510

Met Lys Val Ser Ile Cys Leu Pro Met Asp Ile Asp Ser Pro Leu Ser
                515                 520                 525

Gln Leu Tyr Val Met Ser Leu Leu Val Leu Asn Val Leu Ala Phe Val
                530                 535                 540

Val Ile Cys Gly Cys Tyr Ala His Ile Tyr Leu Thr Val Arg Asn Pro
545                 550                 555                 560

Asn Ile Val Ser Ser Ser Asp Thr Lys Ile Ala Lys Arg Met Ala
                565                 570                 575

Met Leu Ile Phe Thr Asp Phe Leu Cys Met Ala Pro Ile Ser Phe Phe
                580                 585                 590

Ala Ile Ser Ala Ser Leu Lys Val Pro Leu Ile Thr Val Ser Lys Ser
                595                 600                 605

Lys Ile Leu Leu Val Leu Phe Tyr Pro Ile Asn Ser Cys Ala Asn Pro
                610                 615                 620

Phe Leu Tyr Ala Ile Phe Thr Lys Asn Phe Arg Arg Asp Phe Phe Ile
625                 630                 635                 640

Leu Leu Ser Lys Phe Gly Cys Tyr Glu Ile Gln Ala Gln Thr Tyr Arg
                645                 650                 655

Thr Glu Thr Ser Ser Thr Ala His Asn Ser His Pro Arg Asn Gly His
                660                 665                 670

Cys Pro Pro Ala Pro Arg Val Thr Asn Gly Ser Asn Tyr Thr Leu Val
                675                 680                 685

Pro Leu Ser His Leu Ala Gln Asn
690                 695
```